US009951131B2

(12) United States Patent
Barbour et al.

(10) Patent No.: US 9,951,131 B2
(45) Date of Patent: Apr. 24, 2018

(54) ANTIBODIES THAT RECOGNIZE IAPP

(71) Applicant: PROTHENA BIOSCIENCES LIMITED, Dublin (IE)

(72) Inventors: Robin Barbour, Walnut Creek, CA (US); Tarlochan S. Nijjar, Orinda, CA (US)

(73) Assignee: PROTHENA BIOSCIENCES LIMITED, Co. Dublin (IE)

( * ) Notice: Subject to any disclaimer, the term of this patent is extended or adjusted under 35 U.S.C. 154(b) by 366 days.

(21) Appl. No.: 14/329,475

(22) Filed: Jul. 11, 2014

(65) Prior Publication Data
US 2015/0110776 A1 Apr. 23, 2015

Related U.S. Application Data

(60) Provisional application No. 61/845,914, filed on Jul. 12, 2013, provisional application No. 62/014,029, filed on Jun. 18, 2014.

(51) Int. Cl.
*C07K 16/26* (2006.01)
*A61K 39/395* (2006.01)
*G01N 33/66* (2006.01)
*A61K 39/00* (2006.01)

(52) U.S. Cl.
CPC ............ *C07K 16/26* (2013.01); *G01N 33/66* (2013.01); *A61K 2039/505* (2013.01); *C07K 2317/24* (2013.01); *C07K 2317/34* (2013.01); *C07K 2317/92* (2013.01); *Y10T 436/144444* (2015.01)

(58) Field of Classification Search
None
See application file for complete search history.

(56) References Cited

U.S. PATENT DOCUMENTS

| 5,716,619 A * | 2/1998 | Cooper ................ C07K 16/26 424/130.1 |
| 2015/0110777 A1 | 4/2015 | Barbour et al. |
| 2015/0191541 A1 | 7/2015 | Barbour |

FOREIGN PATENT DOCUMENTS

| WO | WO 1989/006135 A1 | 7/1989 |
| WO | WO 1994/004679 A1 | 3/1994 |
| WO | WO 2003/092619 A1 | 11/2003 |
| WO | WO 2015/004632 A1 | 1/2015 |
| WO | WO 2015/004633 A1 | 1/2015 |
| WO | WO 2015/083125 A3 | 6/2015 |

OTHER PUBLICATIONS

Khantasup et al., Monoclonal Antibodies in Immunodiagnosis and Immunotherapy, 2015, 34(6): 404-417.*
PCT/IB2014/066612 Invitation to Pay dated Mar. 3, 2015.
Zhang, et al., "A Novel Antibody Humanization Method Based on Epitopes Scanning and Molecular Dynamics Simulation," *PLOS ONE*, vol. 8, Issue 11 (Nov. 2013).
Almagro, et al., "Humanization of antibodies," *Frontiers Bioscience*, 13:1619-1633 (Jan. 1, 2008).
PCT/IB2014/066612 International Search Report and Written Opinion dated Jun. 16, 2015.
U.S. Appl. No. 14/329,496 Restriction Requirement dated Sep. 26, 2016.
U.S. Appl. No. 14/561,609 Restriction Requirement dated Oct. 28, 2016.
U.S. Appl. No. 14/329,496 Non-Final Office Action dated Mar. 14, 2017.
Colman, "Effects of amino acid sequence changes on antibody-antigen interactions," *Research in Immunology*, 145:33-36, (1994).
Bendig, "Humanization of Rodent Monoclonal Antibodies by CDR Grafting," *Methods: A Companion to Methods in Enzymology*, 8:83-93, (1995).
Berglund et al., "The epitope space of the human proteome," *Protein Science*, 17:606-613, (2008).
Paul, "Structure and Function of Immunoglobins," *Fundamental Immunology*, 3rd Edition, pp. 292-295, (1993).
Rudikoff et al., "Single amino acid substitution altering antigen-binding specificity," *Proc Natl Acad Sci USA*, 79(6):1979-1983, (1982).
"Immunomicroscopy," *Molecular Biomethods Handbook 2nd Edition*, edited by Walker et al., p. 1063, (2008).
Padlan, "X-Ray Crystallography of Antibodies," *Advances in Protein Chemistry*, 49:57-133, (1996).
Tzartos et al., "Epitope Mapping by Antibody Competition: Methodology and Evaluation of the Validity of the Technique," *Methods in Molecular Biology*, 66:55-66, (1996).
U.S. Appl. No. 14/561,609 Non-Final Office Action dated Feb. 15, 2017.
PCT/IB2014/063017 International Preliminary Report on Patentability dated Jan. 12, 2016.
PCT/IB2014/063016 International Preliminary Report on Patentability dated Jan. 12, 2016.

(Continued)

*Primary Examiner* — Hong Sang
(74) *Attorney, Agent, or Firm* — Alston & Bird LLP

(57) ABSTRACT

The invention provides monoclonal antibody 3H6 and related antibodies. The 3H6 antibody binds to an epitope within residues 28-36 of IAPP. The antibodies of the invention are useful, for example, for treating disorders associated with IAPP accumulation, particularly accumulation of IAPP deposits. Such disorders include type 2 diabetes, metabolic syndrome, impaired insulin tolerance, impaired glucose tolerance, insulinomas, and related conditions.

19 Claims, 20 Drawing Sheets
(8 of 20 Drawing Sheet(s) Filed in Color)

(56) References Cited

OTHER PUBLICATIONS

PCT/IB2014/066612 International Preliminary Report on Patentability dated Jun. 7, 2016.
U.S. Appl. No. 14/561,609 Final Rejection dated May 30, 2017.
U.S. Appl. No. 14/329,496 Notice of Allowance and Interview Summary dated Aug. 16, 2017.
U.S. Appl. No. 14/561,609 Advisory Action dated Aug. 8, 2017.

* cited by examiner

3H6 versus isotype control treated HIP Rat Hemoglobin A1c Levels

| Column D | Isotype control |
|---|---|
| vs. | vs. |
| Column A | 3H6 |
|  |  |
| Mann Whitney test |  |
| P value | 0.0069 |
| Exact or approximate P value? | Exact |
| P value summary | ** |
| Significantly different? (P < 0.05) | Yes |
| One- or two-tailed P value? | Two-tailed |
| Sum of ranks in column A,D | 260.5 , 480.5 |
| Mann-Whitney U | 89.50 |

| Column D | Isotype control 180 |
|---|---|
| vs. | vs. |
| Column A | 3H6 180 |
|  |  |
| Mann Whitney test |  |
| P value | <0.0001 |
| Exact or approximate P value? | Exact |
| P value summary | **** |
| Significantly different? (P < 0.05) | Yes |
| One- or two-tailed P value? | Two-tailed |

FIGURE 6A

Humanized 3H6 Vh Regions

| Kabat residue # | Linear residue # | FR or CDR | Parent mouse mAb | Hu VH Acceptor FR, ABI74422.1 | Humanized Design v1 (A78V, T94I) | Humanized Design v2 (NONE) | Humanized Design v3 (T94I) |
|---|---|---|---|---|---|---|---|
| | | | SEQ ID NO: 9 | SEQ ID NO: 13 | SEQ ID NO: 14 | SEQ ID NO: 15 | SEQ ID NO: 16 |
| 1 | 1 | Fr1 | E | L | E | E | E |
| 2 | 2 | Fr1 | V | V | V | V | V |
| 3 | 3 | Fr1 | K | Q | Q | Q | Q |
| 4 | 4 | Fr1 | L | L | L | L | L |
| 5 | 5 | Fr1 | E | V | V | V | V |
| 6 | 6 | Fr1 | E | E | E | E | E |
| 7 | 7 | Fr1 | S | S | S | S | S |
| 8 | 8 | Fr1 | G | G | G | G | G |
| 9 | 9 | Fr1 | G | G | G | G | G |
| 10 | 10 | Fr1 | G | G | G | G | G |
| 11 | 11 | Fr1 | L | L | L | L | L |
| 12 | 12 | Fr1 | V | V | V | V | V |
| 13 | 13 | Fr1 | Q | Q | Q | Q | Q |
| 14 | 14 | Fr1 | P | P | P | P | P |
| 15 | 15 | Fr1 | G | G | G | G | G |
| 16 | 16 | Fr1 | G | G | G | G | G |
| 17 | 17 | Fr1 | S | S | S | S | S |
| 18 | 18 | Fr1 | M | L | L | L | L |
| 19 | 19 | Fr1 | K | K | K | K | K |
| 20 | 20 | Fr1 | L | L | L | L | L |
| 21 | 21 | Fr1 | S | S | S | S | S |
| 22 | 22 | Fr1 | C | C | C | C | C |
| 23 | 23 | Fr1 | V | A | A | A | A |
| 24 | 24 | Fr1 | A | A | A | A | A |
| 25 | 25 | Fr1 | S | S | S | S | S |
| 26 | 26 | Fr1 | G | G | G | G | G |
| 27 | 27 | Fr1 | F | F | F | F | F |
| 28 | 28 | Fr1 | T | T | T | T | T |
| 29 | 29 | Fr1 | F | F | F | F | F |

FIGURE 6B

Humanized 3H6 Vh Regions

| Kabat residue # | Linear residue # | FR or CDR | Parent mouse mAb SEQ ID NO: 9 | Hu VH Acceptor FR, AB174422.1 SEQ ID NO: 13 | Humanized Design v1 (A78V, T94I) SEQ ID NO: 14 | Humanized Design v2 (NONE) SEQ ID NO: 15 | Humanized Design v3 (T94I) SEQ ID NO: 16 |
|---|---|---|---|---|---|---|---|
| 30 | 30 | Fr1 | S | S | S | S | S |
| 31 | 31 | CDR-H1 | N | G | N | N | N |
| 32 | 32 | CDR-H1 | Y | S | Y | Y | Y |
| 33 | 33 | CDR-H1 | W | A | W | W | W |
| 34 | 34 | CDR-H1 | M | M | M | M | M |
| 35 | 35 | CDR-H1 | Y | H | Y | Y | Y |
| 35A | | CDR-H1 | | | | | |
| 35B | | CDR-H1 | | | | | |
| 36 | 36 | Fr2 | W | W | W | W | W |
| 37 | 37 | Fr2 | V | V | V | V | V |
| 38 | 38 | Fr2 | R | R | R | R | R |
| 39 | 39 | Fr2 | Q | Q | Q | Q | Q |
| 40 | 40 | Fr2 | S | A | A | A | A |
| 41 | 41 | Fr2 | P | S | P | P | P |
| 42 | 42 | Fr2 | E | G | G | G | G |
| 43 | 43 | Fr2 | K | K | K | K | K |
| 44 | 44 | Fr2 | G | G | G | G | G |
| 45 | 45 | Fr2 | L | L | L | L | L |
| 46 | 46 | Fr2 | E | E | E | E | E |
| 47 | 47 | Fr2 | W | W | W | W | W |
| 48 | 48 | Fr2 | V | V | V | V | V |
| 49 | 49 | Fr2 | A | G | G | G | G |
| 50 | 50 | CDR-H2 | E | R | E | E | E |
| 51 | 51 | CDR-H2 | I | I | I | I | I |
| 52 | 52 | CDR-H2 | R | R | R | R | R |
| 52A | 53 | CDR-H2 | L | S | L | L | L |
| 52B | 54 | CDR-H2 | K | K | K | K | K |
| 52C | 55 | CDR-H2 | S | A | S | S | S |
| 53 | 56 | CDR-H2 | D | N | D | D | D |
| 54 | 57 | CDR-H2 | N | S | N | N | N |

FIGURE 6C

Humanized 3H6 Vh Regions

| Kabat residue # | Linear residue # | FR or CDR | Parent mouse mAb SEQ ID NO: 9 | Hu VH Acceptor FR, ABI74422.1 SEQ ID NO: 13 | Humanized Design v1 (A78V, T94I) SEQ ID NO: 14 | Humanized Design v2 (NONE) SEQ ID NO: 15 | Humanized Design v3 (T94I) SEQ ID NO: 16 |
|---|---|---|---|---|---|---|---|
| 55 | 58 | CDR-H2 | Y | Y | Y | Y | Y |
| 56 | 59 | CDR-H2 | A | A | A | A | A |
| 57 | 60 | CDR-H2 | T | T | T | T | T |
| 58 | 61 | CDR-H2 | H | A | H | H | H |
| 59 | 62 | CDR-H2 | Y | Y | Y | Y | Y |
| 60 | 63 | CDR-H2 | A | A | A | A | A |
| 61 | 64 | CDR-H2 | E | A | E | E | E |
| 62 | 65 | CDR-H2 | S | S | S | S | S |
| 63 | 66 | CDR-H2 | V | V | V | V | V |
| 64 | 67 | CDR-H2 | K | K | K | K | K |
| 65 | 68 | CDR-H2 | G | G | G | G | G |
| 66 | 69 | Fr3 | R | R | R | R | R |
| 67 | 70 | Fr3 | F | F | F | F | F |
| 68 | 71 | Fr3 | T | T | T | T | T |
| 69 | 72 | Fr3 | I | I | I | I | I |
| 70 | 73 | Fr3 | S | S | S | S | S |
| 71 | 74 | Fr3 | R | R | R | R | R |
| 72 | 75 | Fr3 | D | D | D | D | D |
| 73 | 76 | Fr3 | D | D | D | D | D |
| 74 | 77 | Fr3 | S | S | S | S | S |
| 75 | 78 | Fr3 | K | K | K | K | K |
| 76 | 79 | Fr3 | S | N | N | N | N |
| 77 | 80 | Fr3 | S | T | T | T | T |
| 78 | 81 | Fr3 | V | A | V | A | A |
| 79 | 82 | Fr3 | Y | Y | Y | Y | Y |
| 80 | 83 | Fr3 | L | L | L | L | L |
| 81 | 84 | Fr3 | Q | Q | Q | Q | Q |
| 82 | 85 | Fr3 | M | M | M | M | M |
| 82A | 86 | Fr3 | N | D | D | D | D |
| 82B | 87 | Fr3 | S | S | S | S | S |

FIGURE 6D

Humanized 3H6 Vh Regions

| Kabat residue # | Linear residue # | FR or CDR | Parent mouse mAb SEQ ID NO: 9 | Hu VH Acceptor FR, ABI74422 .1 SEQ ID NO: 13 | Humanized Design v1 (A78V, T94I) SEQ ID NO: 14 | Humanized Design v2 (NONE) SEQ ID NO: 15 | Humanized Design v3 (T94I) SEQ ID NO: 16 |
|---|---|---|---|---|---|---|---|
| 82C | 88 | Fr3 | L | L | L | L | L |
| 83 | 89 | Fr3 | R | K | K | K | K |
| 84 | 90 | Fr3 | A | T | T | T | T |
| 85 | 91 | Fr3 | E | E | E | E | E |
| 86 | 92 | Fr3 | D | D | D | D | D |
| 87 | 93 | Fr3 | T | T | T | T | T |
| 88 | 94 | Fr3 | G | A | A | A | A |
| 89 | 95 | Fr3 | I | V | V | V | V |
| 90 | 96 | Fr3 | Y | Y | Y | Y | Y |
| 91 | 97 | Fr3 | Y | Y | Y | Y | Y |
| 92 | 98 | Fr3 | C | C | C | C | C |
| 93 | 99 | Fr3 | T | T | T | T | T |
| 94 | 100 | Fr3 | I | T | I | T | I |
| 95 | 101 | CDR-H3 | F | Y | F | F | F |
| 96 | 102 | CDR-H3 | D | E | D | D | D |
| 97 | 103 | CDR-H3 | Y | G | Y | Y | Y |
| 98 | | CDR-H3 | | | | | |
| 99 | | CDR-H3 | | | | | |
| 100 | | CDR-H3 | | | | | |
| 100A | | CDR-H3 | | | | | |
| 100B | | CDR-H3 | | | | | |
| 100C | | CDR-H3 | | | | | |
| 100D | | CDR-H3 | | | | | |
| 100E | | CDR-H3 | | | | | |
| 100F | | CDR-H3 | | | | | |
| 100G | | CDR-H3 | | | | | |
| 100H | | CDR-H3 | | | | | |
| 100I | | CDR-H3 | | | | | |
| 100J | | CDR-H3 | | | | | |
| 100K | | CDR-H3 | | | | | |

FIGURE 6E

Humanized 3H6 Vh Regions

| Kabat residue # | Linear residue # | FR or CDR | Parent mouse mAb | Hu VH Acceptor FR, ABI74422.1 | Humanized Design v1 (A78V, T94I) | Humanized Design v2 (NONE) | Humanized Design v3 (T94I) |
|---|---|---|---|---|---|---|---|
| | | | SEQ ID NO: 9 | SEQ ID NO: 13 | SEQ ID NO: 14 | SEQ ID NO: 15 | SEQ ID NO: 16 |
| 101 | | CDR-H3 | | | | | |
| 102 | | CDR-H3 | | | | | |
| 103 | 104 | Fr4 | W | W | W | W | W |
| 104 | 105 | Fr4 | G | G | G | G | G |
| 105 | 106 | Fr4 | Q | Q | Q | Q | Q |
| 106 | 107 | Fr4 | G | G | G | G | G |
| 107 | 108 | Fr4 | T | T | T | T | T |
| 108 | 109 | Fr4 | T | L | L | L | L |
| 109 | 110 | Fr4 | V | V | V | V | V |
| 110 | 111 | Fr4 | T | T | T | T | T |
| 111 | 112 | Fr4 | V | V | V | V | V |
| 112 | 113 | Fr4 | S | S | S | S | S |
| 113 | 114 | Fr4 | S | S | S | S | S |

FIGURE 7A

Humanized 3H6 Vk Regions

| Kabat residue # | Linear residue # | FR or CDR | Parent mouse mAb SEQ ID NO: 20 | Hu VL Acceptor Fr Acc# S23230 SEQ ID NO: 24 | Humanized Design v1 (F36L, R45K, Y86H) SEQ ID NO: 25 | Humanized Design v2 (F36L, R45K) SEQ ID NO: 26 | Humanized Design v3 (NONE) SEQ ID NO: 27 | Humanized Design v4 (R45K, Y86H) SEQ ID NO: 28 |
|---|---|---|---|---|---|---|---|---|
| 1 | 1 | Fr1 | D | D | D | D | D | D |
| 2 | 2 | Fr1 | V | V | V | V | V | V |
| 3 | 3 | Fr1 | V | V | V | V | V | V |
| 4 | 4 | Fr1 | M | M | M | M | M | M |
| 5 | 5 | Fr1 | T | T | T | T | T | T |
| 6 | 6 | Fr1 | Q | Q | Q | Q | Q | Q |
| 7 | 7 | Fr1 | T | S | S | S | S | S |
| 8 | 8 | Fr1 | P | P | P | P | P | P |
| 9 | 9 | Fr1 | L | L | L | L | L | L |
| 10 | 10 | Fr1 | T | S | S | S | S | S |
| 11 | 11 | Fr1 | L | L | L | L | L | L |
| 12 | 12 | Fr1 | S | P | P | P | P | P |
| 13 | 13 | Fr1 | V | V | V | V | V | V |
| 14 | 14 | Fr1 | T | T | T | T | T | T |
| 15 | 15 | Fr1 | I | L | L | L | L | L |
| 16 | 16 | Fr1 | G | G | G | G | G | G |
| 17 | 17 | Fr1 | Q | Q | Q | Q | Q | Q |
| 18 | 18 | Fr1 | P | P | P | P | P | P |
| 19 | 19 | Fr1 | A | A | A | A | A | A |
| 20 | 20 | Fr1 | S | S | S | S | S | S |
| 21 | 21 | Fr1 | I | I | I | I | I | I |
| 22 | 22 | Fr1 | S | S | S | S | S | S |
| 23 | 23 | Fr1 | C | C | C | C | C | C |
| 24 | 24 | CDR-L1 | K | R | K | K | K | K |
| 25 | 25 | CDR-L1 | S | S | S | S | S | S |
| 26 | 26 | CDR-L1 | S | S | S | S | S | S |
| 27 | 27 | CDR-L1 | Q | Q | Q | Q | Q | Q |
| 27A | 28 | CDR-L1 | S | S | S | S | S | S |
| 27B | 29 | CDR-L1 | L | L | L | L | L | L |

FIGURE 7B

Humanized 3H6 Vk Regions

| Kabat residue # | Linear residue # | FR or CDR | Parent mouse mAb SEQ ID NO: 20 | Hu VL Acceptor Fr Acc# S23230 SEQ ID NO: 24 | Humanized Design v1 (F36L, R45K, Y86H) SEQ ID NO: 25 | Humanized Design v2 (F36L, R45K) SEQ ID NO: 26 | Humanized Design v3 (NONE) SEQ ID NO: 27 | Humanized Design v4 (R45K, Y86H) SEQ ID NO: 28 |
|---|---|---|---|---|---|---|---|---|
| 27C | 30 | CDR-L1 | L | V | L | L | L | L |
| 27D | 31 | CDR-L1 | D | Y | D | D | D | D |
| 27E | 32 | CDR-L1 | S | S | S | S | S | S |
| 27F |  | CDR-L1 | — |  | — |  |  |  |
| 28 | 33 | CDR-L1 | D | D | D | D | D | D |
| 29 | 34 | CDR-L1 | G | G | G | G | G | G |
| 30 | 35 | CDR-L1 | K | N | K | K | K | K |
| 31 | 36 | CDR-L1 | T | T | T | T | T | T |
| 32 | 37 | CDR-L1 | Y | H | Y | Y | Y | Y |
| 33 | 38 | CDR-L1 | L | L | L | L | L | L |
| 34 | 39 | CDR-L1 | N | N | N | N | N | N |
| 35 | 40 | Fr2 | W | W | W | W | W | W |
| 36 | 41 | Fr2 | L | F | L | L | F | F |
| 37 | 42 | Fr2 | L | Q | Q | Q | Q | Q |
| 38 | 43 | Fr2 | Q | Q | Q | Q | Q | Q |
| 39 | 44 | Fr2 | R | R | R | R | R | R |
| 40 | 45 | Fr2 | P | P | P | P | P | P |
| 41 | 46 | Fr2 | G | G | G | G | G | G |
| 42 | 47 | Fr2 | Q | Q | Q | Q | Q | Q |
| 43 | 48 | Fr2 | S | S | S | S | S | S |
| 44 | 49 | Fr2 | P | P | P | P | P | P |
| 45 | 50 | Fr2 | K | R | K | K | R | K |
| 46 | 51 | Fr2 | R | R | R | R | R | R |
| 47 | 52 | Fr2 | L | L | L | L | L | L |
| 48 | 53 | Fr2 | I | I | I | I | I | I |
| 49 | 54 | Fr2 | Y | Y | Y | Y | Y | Y |
| 50 | 55 | CDR-L2 | L | K | L | L | L | L |
| 51 | 56 | CDR-L2 | V | V | V | V | V | V |
| 52 | 57 | CDR-L2 | S | S | S | S | S | S |

FIGURE 7C

Humanized 3H6 Vk Regions

| Kabat residue # | Linear residue # | FR or CDR | Parent mouse mAb SEQ ID NO: 20 | Hu VL Acceptor Fr Acc# S23230 SEQ ID NO: 24 | Humanized Design v1 (F36L, R45K, Y86H) SEQ ID NO: 25 | Humanized Design v2 (F36L, R45K) SEQ ID NO: 26 | Humanized Design v3 (NONE) SEQ ID NO: 27 | Humanized Design v4 (R45K, Y86H) SEQ ID NO: 28 |
|---|---|---|---|---|---|---|---|---|
| 53 | 58 | CDR-L2 | K | N | K | K | K | K |
| 54 | 59 | CDR-L2 | L | R | L | L | L | L |
| 55 | 60 | CDR-L2 | D | D | D | D | D | D |
| 56 | 61 | CDR-L2 | S | S | S | S | S | S |
| 57 | 62 | Fr3 | G | G | G | G | G | G |
| 58 | 63 | Fr3 | V | V | V | V | V | V |
| 59 | 64 | Fr3 | P | P | P | P | P | P |
| 60 | 65 | Fr3 | D | D | D | D | D | D |
| 61 | 66 | Fr3 | R | R | R | R | R | R |
| 62 | 67 | Fr3 | F | F | F | F | F | F |
| 63 | 68 | Fr3 | T | S | S | S | S | S |
| 64 | 69 | Fr3 | G | G | G | G | G | G |
| 65 | 70 | Fr3 | S | S | S | S | S | S |
| 66 | 71 | Fr3 | G | G | G | G | G | G |
| 67 | 72 | Fr3 | S | S | S | S | S | S |
| 68 | 73 | Fr3 | G | G | G | G | G | G |
| 69 | 74 | Fr3 | T | T | T | T | T | T |
| 70 | 75 | Fr3 | D | D | D | D | D | D |
| 71 | 76 | Fr3 | F | F | F | F | F | F |
| 72 | 77 | Fr3 | T | T | T | T | T | T |
| 73 | 78 | Fr3 | L | L | L | L | L | L |
| 74 | 79 | Fr3 | K | K | K | K | K | K |
| 75 | 80 | Fr3 | I | I | I | I | I | I |
| 76 | 81 | Fr3 | S | S | S | S | S | S |
| 77 | 82 | Fr3 | R | R | R | R | R | R |
| 78 | 83 | Fr3 | V | V | V | V | V | V |
| 79 | 84 | Fr3 | E | E | E | E | E | E |
| 80 | 85 | Fr3 | A | A | A | A | A | A |
| 81 | 86 | Fr3 | E | E | E | E | E | E |

FIGURE 7D

Humanized 3H6 Vk Regions

| Kabat residue # | Linear residue # | FR or CDR | Parent mouse mAb SEQ ID NO: 20 | Hu VL Acceptor Fr Acc# S23230 SEQ ID NO: 24 | Humanized Design v1 (F36L, R45K, Y86H) SEQ ID NO: 25 | Humanized Design v2 (F36L, R45K) SEQ ID NO: 26 | Humanized Design v3 (NONE) SEQ ID NO: 27 | Humanized Design v4 (R45K, Y86H) SEQ ID NO: 28 |
|---|---|---|---|---|---|---|---|---|
| 82 | 87 | Fr3 | D | D | D | D | D | D |
| 83 | 88 | Fr3 | L | V | V | V | V | V |
| 84 | 89 | Fr3 | G | G | G | G | G | G |
| 85 | 90 | Fr3 | V | V | V | V | V | V |
| 86 | 91 | Fr3 | H | Y | H | Y | Y | H |
| 87 | 92 | Fr3 | Y | Y | Y | Y | Y | Y |
| 88 | 93 | Fr3 | C | C | C | C | C | C |
| 89 | 94 | CDR-L3 | W | M | W | W | W | W |
| 90 | 95 | CDR-L3 | Q | Q | Q | Q | Q | Q |
| 91 | 96 | CDR-L3 | G | G | G | G | G | G |
| 92 | 97 | CDR-L3 | R | T | R | R | R | R |
| 93 | 98 | CDR-L3 | H | H | H | H | H | H |
| 94 | 99 | CDR-L3 | F | W | F | F | F | F |
| 95 | 100 | CDR-L3 | P | P | P | P | P | P |
| 95A | | CDR-L3 | | | | | | |
| 95B | | CDR-L3 | | | | | | |
| 95C | | CDR-L3 | | | | | | |
| 95D | | CDR-L3 | | | | | | |
| 95E | | CDR-L3 | | | | | | |
| 95F | | CDR-L3 | | | | | | |
| 96 | 101 | CDR-L3 | Y | Y | Y | Y | Y | Y |
| 97 | 102 | CDR-L3 | T | T | T | T | T | T |
| 98 | 103 | Fr4 | F | F | F | F | F | F |
| 99 | 104 | Fr4 | G | G | G | G | G | G |
| 100 | 105 | Fr4 | G | Q | Q | Q | Q | Q |
| 101 | 106 | Fr4 | G | G | G | G | G | G |
| 102 | 107 | Fr4 | T | T | T | T | T | T |
| 103 | 108 | Fr4 | K | K | K | K | K | K |
| 104 | 109 | Fr4 | L | L | L | L | L | L |

FIGURE 7E

Humanized 3H6 Vk Regions

| Kabat residue # | Linear residue # | FR or CDR | Parent mouse mAb | Hu VL Acceptor Fr Acc# S23230 | Humanized Design v1 (F36L, R45K, Y86H) | Humanized Design v2 (F36L, R45K) | Humanized Design v3 (NONE) | Humanized Design v4 (R45K, Y86H) |
|---|---|---|---|---|---|---|---|---|
| | | | SEQ ID NO: 20 | SEQ ID NO: 24 | SEQ ID NO: 25 | SEQ ID NO: 26 | SEQ ID NO: 27 | SEQ ID NO: 28 |
| 105 | 110 | Fr4 | E | E | E | E | E | E |
| 106 | 111 | Fr4 | I | I | I | I | I | I |
| 106A | | Fr4 | | | | | | |
| 107 | 112 | Fr4 | K | K | K | K | K | K |

ANTIBODIES THAT RECOGNIZE IAPP

CROSS REFERENCE TO RELATED APPLICATIONS

This application claims the benefit of U.S. Provisional Patent Application No. 61/845,914, filed Jul. 12, 2013, and U.S. Provisional Patent Application No. 62/014,029, filed Jun. 18, 2014, both of which are incorporated by reference in their entirety for all purposes.

REFERENCE TO A SEQUENCE LISTING

The Sequence Listing written in file 447787SEQLIST.txt is 43.4 kilobytes, was created on Jul. 10, 2014, and is hereby incorporated by reference.

BACKGROUND

Several diseases are thought to be caused by the abnormal folding and aggregation of disease-specific proteins. These proteins can accumulate into pathologically diagnostic accumulations, known as amyloids, which are visualized by certain histologic stains. Amyloids are thought to elicit inflammatory responses and have multiple negative consequences for the involved tissues. In addition, smaller aggregates of abnormally folded protein may exist and exert cytotoxic effects.

Type-2 diabetes (T2D) is a common disease where amyloid accumulations are often seen in the pancreas. The amyloid accumulations include islet-amyloid polypeptide (IAPP), also known as amylin. Accumulating evidence associates toxic IAPP oligomers and IAPP deposits with T2D. See, e.g., Haataja et al. (2008), Islet amyloid in type 2 diabetes, and the toxic oligomer hypothesis, Endocrine Reviews 29:303-316. For example, there is evidence of the involvement of toxic IAPP oligomers in p-cell apoptosis in T2D. See Janson et al. (1999), The mechanism of islet amyloid polypeptide toxicity is membrane disruption by intermediate-sized toxic amyloid particles, Diabetes 48:491-498; Lorenzo et al. (1994), Pancreatic islet cell toxicity of amylin associated with type-2 diabetes mellitus, Nature 368:756-760; Ritzel & Butler (2003), Replication increases beta-cell vulnerability to human islet amyloid polypeptide-induced apoptosis, Diabetes 52:1701-1708. In addition, humans, monkeys and cats express an amyloidogenic toxic form of IAPP and develop diabetes characterized by islet amyloid deposits. See O'Brien et al. (1993), Islet amyloid polypeptide: A review of its biology and potential roles in the pathogenesis of diabetes mellitus, Vet. Pathol. 30:317-332. IAPP deposits are also found in insulinomas. See O'Brien et al. (1994), Islet amyloid polypeptide in human insulinomas. Evidence for intracellular amyloidogenesis, Diabetes 43: 329-336.

Pre-diabetes is a condition in which individuals have blood glucose levels higher than normal but not high enough to be classified as diabetes. People with pre-diabetes have an increased risk of developing T2D. People with pre-diabetes have impaired fasting glucose ("IFG") or impaired glucose tolerance ("IGT"), and some people have both IFG and IGT (National Diabetes Statistics, 2007).

SUMMARY OF THE CLAIMED INVENTION

In one aspect, the invention provides an isolated monoclonal antibody that binds to an epitope within human IAPP, such as an epitope within amino acid residues 28-36. The antibody can compete with monoclonal antibody 3H6 for binding to human IAPP and/or bind to the same epitope as monoclonal antibody 3H6. Subjects receiving such an antibody (e.g., subjects having or are at risk of a condition associated with IAPP accumulation) preferably have lower blood glucose levels following oral glucose challenge relative to control subjects who did not receive the antibody or who received a control antibody. Preferably, the antibody is chimeric, veneered, humanized or human. The antibody can be of human IgG1 isotype. Alternatively, the antibody can be of human IgG2 or IgG4 isotype. The antibody can include at least one mutation (e.g., one or more mutations) in a constant region. The antibody can be an antigen-binding fragment, such as a Fab fragment or a single-chain Fv antibody.

In another aspect, the invention provides an antibody that includes three light chain CDRs (as defined by Kabat) and three heavy chain CDRs (as defined by Kabat) of monoclonal antibody 3H6. Subjects receiving such an antibody (e.g., subjects having or are at risk of a condition associated with IAPP accumulation) preferably have lower blood glucose levels following oral glucose challenge relative to control subjects who did not receive the antibody or who received a control antibody. Preferably, the antibody is chimeric, veneered, or humanized. The antibody can be of human IgG1 isotype. Alternatively, the antibody can be of human IgG2 or IgG4 isotype. The antibody can include at least one mutation (e.g., one or more mutations) in a constant region. The antibody can be an antigen-binding fragment, such as a Fab fragment or a single-chain Fv antibody.

In another aspect, the invention provides an antibody comprising a mature heavy chain variable region having an amino acid sequence at least 90% identical (e.g., at least 95%, 98%, 99%, or 100% identical) to H1 (SEQ ID NO: 14) and a mature light chain variable region having an amino acid sequence at least 90% identical (e.g., at least 95%, 98%, 99%, or 100% identical) to L1 (SEQ ID NO: 25), wherein the antibody specifically binds to human IAPP. The antibody can include three Kabat CDRs of SEQ ID NO: 9 and three Kabat CDRs of SEQ ID NO: 20. In some antibodies, any differences in CDRs of the mature heavy chain variable region and mature light chain variable region from H1 and L1 (SEQ ID NOS: 14 and 25, respectively) reside in positions H60-H65. In some antibodies, at least one of positions H78 and H94 in the heavy chain variable region (Kabat numbering) is occupied by V and I, respectively, and/or at least one of positions L36, L45, and L86 in the light chain variable region (Kabat numbering) is occupied by L, K, and H, respectively. In some antibodies, positions H78 and H94 are occupied by V and I, respectively, and positions L36, L45, and L86 are occupied by L, K, and H, respectively. In some antibodies, position H94 is occupied by I, and at least one of positions L36, L45, and L86 is occupied by L, K, and H, respectively. In some antibodies, position H94 is occupied by I, and positions L36 and L45 are occupied by L and K, respectively. In some antibodies, positions L36, L45, and L86 are occupied by L, K, and H, respectively.

In some antibodies, the mature heavy chain variable region has an amino acid sequence designated H1 (SEQ ID NO: 14) and the mature light chain variable region has an amino acid sequence designated L1 (SEQ ID NO: 25). In other antibodies, the mature heavy chain variable region has an amino acid sequence designated H2 (SEQ ID NO: 15) and the mature light chain variable region has an amino acid sequence designated L1 (SEQ ID NO: 25). In still other antibodies, the mature heavy chain variable region has an amino acid sequence designated H3 (SEQ ID NO: 16) and the mature light chain variable region has an amino acid sequence designated L2 (SEQ ID NO: 26).

In some antibodies, the mature heavy chain variable region is fused to a heavy chain constant region and/or the mature light chain variable region is fused to a light chain constant region. The heavy chain constant region can be a mutant form of a natural human heavy chain constant region which has reduced binding to an Fcγ receptor relative to the natural human heavy chain constant region. The heavy chain constant region can be of IgG1 isotype. In some antibodies, the mature heavy chain variable region is fused to a heavy chain constant region having the sequence of SEQ ID NO: 34 and/or the mature light chain variable region is fused to a light chain constant region having the sequence of SEQ ID NO: 36. In some antibodies, the mature heavy chain variable region is fused to a heavy chain constant region having the sequence of SEQ ID NO: 34, 69, or 70 and/or the mature light chain variable region is fused to a light chain constant region having the sequence of SEQ ID NO: 36 or 72. Alternatively, the antibody can be an antigen-binding fragment, such as a Fab fragment.

Any antibody of the invention can be provided in pure form (e.g., at least 95% w/w pure).

In another aspect, the invention provides pharmaceutical compositions that include an antibody of the invention and a pharmaceutically-acceptable carrier.

In another aspect, the invention provides a nucleic acid encoding the heavy and/or light chain(s) of an antibody of the invention, such as an antibody comprising a mature heavy chain variable region having an amino acid sequence at least 90% identical (e.g., at least 95%, 98%, 99%, or 100% identical) to H1 (SEQ ID NO: 14) and a mature light chain variable region having an amino acid sequence at least 90% identical (e.g., at least 95%, 98%, 99%, or 100% identical) to L1 (SEQ ID NO: 25), wherein the antibody specifically binds to human IAPP. For example, the heavy chain can be encoded by the nucleic acid sequence of SEQ ID NO: 17 and/or the light chain can be encoded by the nucleic acid sequence of SEQ ID NO: 29.

In another aspect, the invention provides a recombinant expression vector comprising a nucleic acid encoding the heavy and/or light chain(s) of an antibody of the invention.

In another aspect, the invention provides a host cell transformed with a nucleic acid of the invention and/or a recombinant expression vector of the invention.

In another aspect, the invention provides a method of humanizing an antibody, particularly a mouse 3H6 antibody such as disclosed herein. The method can include: determining the sequences of the heavy and light chain variable regions of a mouse antibody; synthesizing a nucleic acid encoding a humanized heavy chain comprising CDRs of the mouse antibody heavy chain and a nucleic acid encoding a humanized light chain comprising CDRs of the mouse antibody light chain; and expressing the nucleic acids in a host cell to produce a humanized antibody.

In another aspect, the invention provides a method of producing a humanized, chimeric, or veneered form of the mouse 3H6 antibody disclosed herein. The method can include: culturing cells transformed with nucleic acids encoding the heavy and light chains of the humanized, chimeric, or veneered antibody, so that the cell secretes the antibody; and purifying the antibody from cell culture media.

In another aspect, the invention provides a method of producing a cell line that produces a humanized, chimeric, or veneered form of the mouse 3H6 antibody disclosed herein. The method can include: introducing a vector encoding heavy and light chains of a humanized, chimeric, or veneered 3H6 antibody and a selectable marker into cells; propagating the cells under conditions to select for cells having increased copy number of the vector; isolating single cells from the selected cells; and banking cells cloned from a single cell selected based on yield of antibody.

In another aspect, the invention provides a method of making an antibody. The method can include: obtaining a host cell of the invention; and maintaining the host cell under conditions in which the antibody is expressed. The method can further include collecting the antibody.

In another aspect, the invention provides a method of testing one or more antibodies, particularly an anti-IAPP antibody of the invention, as potential therapeutics. For each anti-IAPP test antibody, the method can include: administering the test antibody to one or more transgenic rodents producing human IAPP ("IAPP transgenic rodents"); performing an oral glucose tolerance test on the one or more IAPP transgenic rodents; and comparing blood glucose levels in the IAPP transgenic rodents receiving the test antibody to blood glucose levels in control IAPP transgenic rodents that did not receive any antibody or that received a control antibody; and selecting the test antibody for development as a potential therapeutic if the blood glucose levels in IAPP transgenic rodents receiving the test antibody are significantly lower than the blood glucose levels in the control IAPP transgenic rodents. The antibody can be a 3H6 antibody. The development can include humanization of the test antibody. The IAPP transgenic rodent can be a HIP rat.

In some methods, 10 mg/kg of test antibody is administered to each rodent weekly. The test antibody can be administered for a period of at least 5, 10, 15, 16, 17, 18, 19, 20, 21, 22, 23, 24, 25, 26, 27, 28, 29, or 30 weeks. In some methods, control rodents are administered a control antibody according to the same schedule as the test antibody is administered to the rodents. Preferably, the control antibody has the same isotype as the test antibody.

In some methods, blood glucose levels are determined 120 minutes after glucose administration during the oral glucose tolerance test. In some methods, blood glucose levels are determined 30, 60, 90, 120, and/or 180 minutes after glucose administration during the oral glucose tolerance test.

In another aspect, the invention provides a method of reducing islet amyloid polypeptide (IAPP) accumulation in a subject having or at risk of a condition associated with IAPP accumulation. The method can include administering to the subject an effective regime of an antibody of the invention (e.g., a humanized or chimeric 3H6 antibody), thereby reducing IAPP accumulation in the subject.

In another aspect, the invention provides a method of inhibiting aggregation of islet amyloid polypeptide (IAPP) in a subject having or at risk of a condition associated with IAPP accumulation. The method can include administering to the subject an effective regime of an antibody of the invention (e.g., a humanized or chimeric 3H6 antibody), thereby inhibiting aggregation of IAPP in the subject.

In another aspect, the invention provides a method of stabilizing a non-toxic conformation of islet amyloid polypeptide (IAPP) in a subject having or at risk of a condition associated with IAPP accumulation. The method can include administering to the subject an effective regime of an antibody of the invention (e.g., a humanized or chimeric 3H6 antibody), thereby stabilizing a non-toxic conformation of IAPP in the subject.

In another aspect, the invention provides a method of reducing islet amyloid polypeptide (IAPP) deposits in a subject having or at risk of developing IAPP deposits. The method can include administering to the subject an effective regime of an antibody of the invention (e.g., a humanized or chimeric 3H6 antibody), thereby reducing IAPP deposits in the subject.

In another aspect, the invention provides a method of clearing aggregated islet amyloid polypeptide in a subject having or at risk of a condition associated with IAPP accumulation. The method can include administering to the subject an effective regime of an antibody of the invention (e.g., a humanized or chimeric 3H6 antibody), thereby clearing aggregated IAPP from the subject.

In another aspect, the invention provides a method of reducing glucose levels in a subject having Type 2 Diabetes (T2D). The method can include administering to the subject an effective regime of an antibody of the invention (e.g., a humanized or chimeric 3H6 antibody), thereby reducing glucose levels in the subject relative to a subject having T2D who has not received the antibody.

In another aspect, the invention provides a method of stabilizing glucose levels in a subject having Type 2 Diabetes (T2D). The method can include administering to the subject an effective regime of an antibody of the invention (e.g., a humanized or chimeric 3H6 antibody), thereby stabilizing glucose levels in the subject. In some methods, the glucose levels are fasting glucose levels. In some methods, the glucose levels are in response to an oral glucose challenge.

In another aspect, the invention provides a method of treating or effecting prophylaxis of a condition associated with IAPP amyloid accumulation in a subject. The method can include administering to the subject an effective regime of an antibody of the invention (e.g., a humanized or chimeric 3H6 antibody). In some methods the condition is associated with amyloid accumulation in the pancreas of the subject. In some methods the condition is type 2 diabetes. In some methods the condition is insulinoma.

In another aspect, the invention provides a method for reducing inflammation associated with IAPP amyloid accumulation in a subject. The method can include administering to the subject an effective amount of an antibody of the invention (e.g., a humanized or chimeric 3H6 antibody). In some methods, the amyloid accumulation is in the pancreas of the subject.

In another aspect, the invention provides a method of reducing, ameliorating or preventing impaired glucose tolerance in a subject having or at risk of a condition associated with IAPP accumulation. The method can include administering to the subject an effective regime of an antibody of the invention (e.g., a humanized or chimeric 3H6 antibody).

In another aspect, the invention provides a method of diagnosing the presence or absence of an IAPP amyloid accumulation in a pancreas of a subject. The method can include contacting a sample from the subject suspected of comprising the amyloid accumulation with an effective amount of an antibody of the invention (e.g., a 3H6 antibody). Some methods also include detecting the binding of antibody to IAPP.

In another aspect, the invention provides a method of determining a level of IAPP deposits in a subject. The method can include: administering an antibody of the invention (e.g., a humanized or chimeric 3H6 antibody); and detecting the presence of bound antibody in the subject. In some methods, the presence of bound antibody is determined by positron emission tomography (PET).

In another aspect, the invention provides a method for delaying the onset of a condition associated with amyloid accumulation in a subject. The method can include administering to the subject an effective amount of a pharmaceutical composition described herein (e.g., a pharmaceutical composition comprising a humanized 3H6 antibody). In some methods, the condition is associated with amyloid accumulation in the pancreas of the subject. In some methods, the condition is type 2 diabetes. In some methods, the condition is insulinoma.

In another aspect, the invention provides a method of reducing beta islet cellular toxicity associated with aggregates or oligomers of IAPP. The method can include administering an effective regime of a pharmaceutical composition described herein (e.g., a pharmaceutical composition comprising a humanized 3H6 antibody).

In another aspect, the invention provides a method of delaying the progression in a subject from pre-diabetes to diabetes. The method can include administering an effective regime of a pharmaceutical composition described herein (e.g., a pharmaceutical composition comprising a humanized 3H6 antibody).

In another aspect, the invention provides a method of ameliorating impaired fasting glucose (IFG) in a subject. The method can include administering an effective regime of a pharmaceutical composition described herein (e.g., a pharmaceutical composition comprising a humanized 3H6 antibody).

In another aspect, the invention provides a method of ameliorating impaired glucose tolerance (IGT) in a subject. The method can include administering an effective regime of a pharmaceutical composition described herein (e.g., a pharmaceutical composition comprising a humanized 3H6 antibody).

In another aspect, the invention provides a method of stabilizing fasting blood glucose levels in a subject at less than 100 milligrams per deciliter after an overnight fast. The method can include administering an effective regime of a pharmaceutical composition described herein (e.g., a pharmaceutical composition comprising a humanized 3H6 antibody).

In another aspect, the invention provides a method of stabilizing blood glucose levels in a subject at less than 140 milligrams per deciliter after a 2-hour oral glucose tolerance test. The method can include administering an effective regime of a pharmaceutical composition described herein (e.g., a pharmaceutical composition comprising a humanized 3H6 antibody).

In another aspect, the invention provides a method of reducing glucose levels in a subject having Type 1 Diabetes (T1D). The method can include administering to the subject an effective regime of an antibody of the invention (e.g., a humanized or chimeric 3H6 antibody), thereby reducing glucose levels in the subject relative to a subject having T1D who has not received the antibody.

In another aspect, the invention provides a method of stabilizing glucose levels in a subject having Type 1.5 Diabetes (T1.5D). The method can include administering to the subject an effective regime of an antibody of the invention (e.g., a humanized or chimeric 3H6 antibody), thereby stabilizing glucose levels in the subject. In some methods, the glucose levels are fasting glucose levels. In some methods, the glucose levels are in response to an oral glucose challenge.

The patent or application file contains at least one drawing executed in color. Copies of this patent or patent application publication with color drawing(s) will be provided by the Office upon request and payment of the necessary fee.

In any of the foregoing methods of treating a subject or detecting IAPP in a subject, the subject can be a human.

BRIEF DESCRIPTION OF THE DRAWINGS

FIGS. 6A-E show humanized 3H6 heavy chain variable region designs and backmutations based on the selected human frameworks.

FIGS. 7A-E show humanized 3H6 light chain variable region designs and backmutations based on the selected human frameworks.

BRIEF DESCRIPTION OF THE SEQUENCES

Figure 1A:
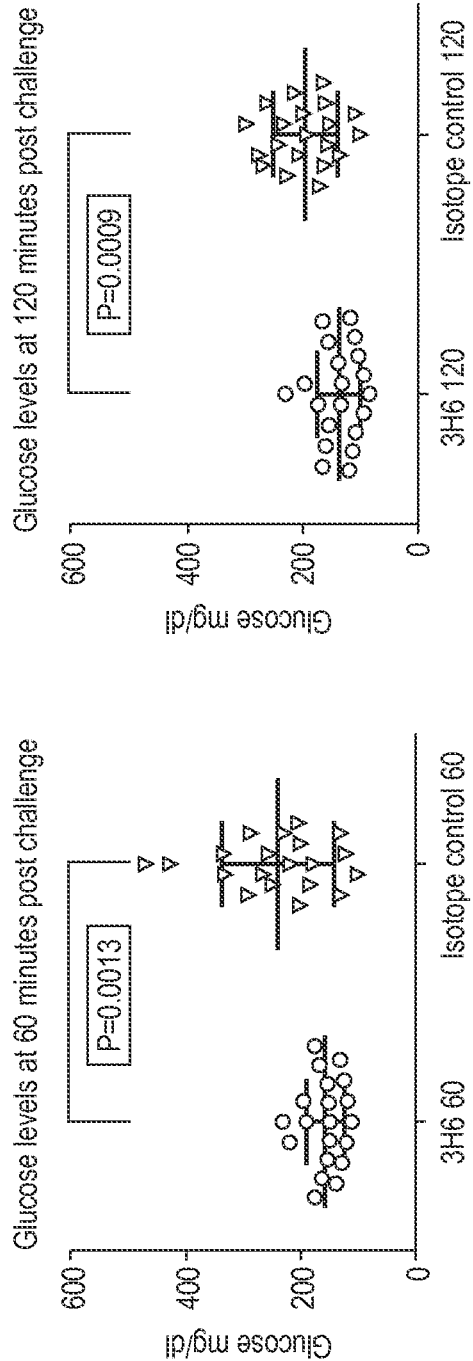
FIG. 1A depicts blood glucose levels in HIP rats that had received treatment with either 3H6 antibody or PS2 isotype control antibody for a period of eighteen weeks. The blood glucose levels were measured as part of an oral glucose challenge test in which 2 g/kg of glucose was ingested after an overnight fast. The individual panels show the blood glucose levels measured at 60 and 120 minutes after administration of glucose.

SEQ ID NO: 1 is the mature human IAPP sequence.
SEQ ID NO: 2 is a peptide for immunization containing amino acid residues 24-35 of hIAPP.
SEQ ID NO: 3 is a peptide for immunization containing amino acid residues 27-37 of hIAPP.
SEQ ID NO: 4 is a peptide corresponding to amino acid residues 27-37 of hIAPP.
SEQ ID NO: 5 is a nucleic acid sequence encoding the 3H6 heavy chain variable region.
SEQ ID NO: 6 is the 3H6 heavy chain variable region sequence, including signal peptide.
SEQ ID NO: 7 is a nucleic acid sequence encoding the 3H6 light chain variable region.
SEQ ID NO: 8 is the 3H6 light chain variable region sequence, including signal peptide.
SEQ ID NO: 9 is the 3H6 mature heavy chain variable region sequence.
SEQ ID NO: 10 is the 3H6 heavy chain CDR1, according to Kabat numbering.
SEQ ID NO: 11 is the 3H6 heavy chain CDR2, according to Kabat numbering.
SEQ ID NO: 12 is the 3H6 heavy chain CDR3, according to Kabat numbering.
SEQ ID NO: 13 is the human VH Acceptor framework of Acc#ABI74422.1.
SEQ ID NO: 14 is the humanized 3H6 H1 sequence.
SEQ ID NO: 15 is the humanized 3H6 H2 sequence.
SEQ ID NO: 16 is the humanized 3H6 H3 sequence.
SEQ ID NO: 17 is a nucleic acid sequence encoding the humanized 3H6 H1 region.
SEQ ID NO: 18 is a nucleic acid sequence encoding the humanized 3H6 H2 region.
SEQ ID NO: 19 is a nucleic acid sequence encoding the humanized 3H6 H3 region.
SEQ ID NO: 20 is the 3H6 mature light chain variable region sequence.
SEQ ID NO: 21 is the 3H6 light chain CDR1, according to Kabat numbering.
SEQ ID NO: 22 is the 3H6 light chain CDR2, according to Kabat numbering.
SEQ ID NO: 23 is the 3H6 light chain CDR3, according to Kabat numbering.
SEQ ID NO: 24 is the human VL acceptor framework, Acc#523230.
SEQ ID NO: 25 is the humanized 3H6 L1 sequence.
SEQ ID NO: 26 is the humanized 3H6 L2 sequence.
SEQ ID NO: 27 is the humanized 3H6 L3 sequence.
SEQ ID NO: 28 is the humanized 3H6 L4 sequence.
SEQ ID NO: 29 is a nucleic acid sequence encoding the humanized 3H6 L1 region.
SEQ ID NO: 30 is a nucleic acid sequence encoding the humanized 3H6 L2 region.
SEQ ID NO: 31 is a nucleic acid sequence encoding the humanized 3H6 L3 region.
SEQ ID NO: 32 is a nucleic acid sequence encoding the humanized 3H6 L4 region.
SEQ ID NO: 33 is a nucleic acid sequence encoding an exemplary human IgG1 constant region.

SEQ ID NO: 34 is an exemplary human IgG1 constant region.

SEQ ID NO: 35 is a nucleic acid sequence encoding an exemplary human kappa light chain constant region without an N-terminal arginine.

SEQ ID NO: 36 is an exemplary human kappa light chain constant region without an N-terminal arginine.

SEQ ID NOS: 37 to 62 and SEQ ID NO: 64 are a sequential series of 11 amino acid peptides from hIAPP, spanning the length of hIAPP in one amino acid increments, each fused to an N-terminally biotinylated Ser-Gly-Ser-Gly linker.

SEQ ID NO: 63 is a peptide containing an N-terminally biotinylated Ser-Gly-Ser-Gly linker fused to amino acid residues 27-37 of hIAPP, with an amidated C-terminal amino acid.

SEQ ID NO: 65 is a peptide corresponding to amino acid residues 1-11 of hIAPP, with a biotinylated C-terminus.

SEQ ID NO: 66 is a peptide corresponding to amino acid residues 27-37 of hIAPP.

SEQ ID NO: 67 is a peptide corresponding to amino acid residues 28-36 of hIAPP.

SEQ ID NO: 68 is a nucleic acid sequence encoding an exemplary human IgG1 constant region of the G1m3 allotype.

SEQ ID NO: 69 is an exemplary human IgG1 constant region of the G1m3 allotype.

SEQ ID NO: 70 is an exemplary human IgG1 constant region of the G1m3 allotype.

SEQ ID NO: 71 is a nucleic acid sequence encoding an exemplary human kappa light chain constant region with an N-terminal arginine.

SEQ ID NO: 72 is an exemplary human kappa light chain constant region with an N-terminal arginine.

DEFINITIONS

The term "antibody" includes intact antibodies and binding fragments thereof. Typically, fragments compete with the intact antibody from which they were derived for specific binding to the target. Fragments include separate heavy chains, separate light chains, Fab, Fab', F(ab')2, F(ab)c, Fv, single chain antibodies, and single domain antibodies. Single (variable) domain antibodies include VH regions separated from their VL partners (or vice versa) in conventional antibodies (Ward et al., 1989, Nature 341: 544-546), as well as VH regions (sometimes known as VHH) from species such as Camelidae or cartilaginous fish (e.g., a nurse shark) in which VH regions are not associated with VL regions (see, e.g., WO 9404678). Single domain antibodies in which one chain is separated from its natural partners are sometimes known as Dabs and single domain antibodies from Camelidae or cartilaginous fish are sometimes known as nanobodies. Constant regions or parts of constant regions may or may not be present in single domain antibodies. For example, natural single variable region antibodies from Camelidae include a VHH variable region, and CH2 and CH3 constant regions. Single domain antibodies, such as nanobodies, can be subject to humanization by analogous approaches to conventional antibodies. Dabs antibodies are usually obtained from antibodies of human origin. Fragments can be produced by recombinant DNA techniques, or by enzymatic or chemical separation of intact immunoglobulins. The term "antibody" also includes a bispecific antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

An "antigen" is an entity to which an antibody specifically binds.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, X-ray crystallography and 2-dimensional nuclear magnetic resonance. See, e.g., Epitope Mapping Protocols, in Methods in Molecular Biology, Vol. 66, Glenn E. Morris, Ed. (1996). An epitope can include a C-terminal residue or an N-terminal residue. An epitope can also include, but need not include, the free amino group of a polypeptide or the free carboxyl group of a polypeptide. Thus, an epitope can include a C-terminal or an N-terminal residue, but not necessarily include the free carboxyl group or the free amino group, respectively. Antibody binding specificity is sometimes defined by a range of amino acids. If an antibody is said to bind to an epitope within amino acids 27-37 of SEQ ID NO: 1, for example, what is meant is that the epitope is within the recited range of amino acids including those defining the outer-limits of the range. It does not necessarily mean that every amino acid within the range constitutes part of the epitope. Thus, for example, an epitope within amino acids 27-37 of SEQ ID NO:1 may consist of amino acids 27-35, 28-32, 28-36, or 33-37, among other segments of SEQ ID NO:1.

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen. See, e.g., Junghans et al. (1990), Cancer Res. 50:1495. A test antibody competes with a reference antibody if an excess of a test antibody (e.g., at least 2×, 5×, 10×, 20× or 100×) inhibits binding of the reference antibody by at least 50%, 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "subject" includes a human and other mammal (e.g., non-human primate, canine, feline, mouse, rat, bovine, equine, and porcine) that receives either prophylactic or therapeutic treatment with an agent such as an antibody or an immunogen.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions (with gaps not counted) multiplied by 100 to convert to percentage.

For purposes of classifying amino acids substitutions as conservative or non-conservative, amino acids are grouped as follows: Group I (hydrophobic side chains): Norleucine, Met, Ala, Val, Leu, Ile; Group II (neutral hydrophilic side chains): Cys, Ser, Thr; Group III (acidic side chains): Asp, Glu; Group IV (basic side chains): Asn, Gln, His, Lys, Arg; Group V (residues influencing chain orientation): Gly, Pro; and Group VI (aromatic side chains): Trp, Tyr, Phe. Conservative substitutions involve substitutions between amino acids in the same class. Non-conservative substitutions constitute exchanging a member of one of these classes for a member of another.

Antibodies of the invention typically bind to their designated target with an affinity constant of at least $10^6$, $10^7$, $10^8$, $10^9$, or $10^{10}$ $M^{-1}$. Such binding is specific binding in that it is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

The term "symptom" refers to subjective evidence of a disease, such as altered gait, as perceived by a subject. A "sign" refers to objective evidence of a disease as observed by a physician.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor. Statistical significance means $p<0.05$.

Monoclonal antibodies and other therapeutic agents (e.g., immunogens) are typically provided in isolated form. This means that the agent is typically at least 50% w/w pure of interfering proteins and other contaminants arising from its production or purification, but does not exclude the possibility that the agent is combined with an excess of pharmaceutically-acceptable carrier(s) or other vehicle intended to facilitate its use. Sometimes monoclonal antibodies are at least 60%, 70%, 80%, 90%, 95%, 96%, 97%, 98%, or 99% w/w pure of aggregates or fragments of such monoclonal antibodies or of other proteins and contaminants. Some such monoclonal antibodies may include aggregates or fragments but are at least 99% w/w pure of other proteins and contaminants.

The basic antibody structural unit is a tetramer of subunits. Each tetramer includes two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. When initially expressed, this variable region is typically linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function. A constant region can include any or all of a CH1 region, hinge region, CH2 region, and CH3 region.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites. Except for bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the regions FR1, CDR1, FR2, CDR2, FR3, CDR3 and FR4. The assignment of amino acids to each region is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number.

A disease, condition, or disorder "associated with IAPP accumulation" or "associated with IAPP amyloid accumulation" refers to a disease, condition, or disorder for which at least one symptom is associated with an abnormal accumulation of a deposit that includes a statistically significant level of IAPP.

"Metabolic syndrome" is a term of art used to describe a disorder comprising combinations of type 2 diabetes, glucose tolerance, impaired insulin sensitivity, hypertension, obesity, increased abdominal girth, hypertriglyceridemia, low HDL, hyperuricaemia, hypercoagulability and/or microalbuminemia. The International Diabetes Federation consensus worldwide definition of the metabolic syndrome (2006) is: Central obesity AND any two of the following: raised triglycerides: >150 mg/dL (1.7 mmol/L), or specific treatment for this lipid abnormality; reduced HDL cholesterol (<40 mg/dL (1.03 mmol/L) in males and <50 mg/dL (1.29 mmol/L) in females), or specific treatment for this lipid abnormality; raised blood pressure (systolic BP>130 or diastolic BP>85 mm Hg), or treatment of previously diagnosed hypertension; raised fasting plasma glucose (FPG) (>100 mg/dL (5.6 mmol/L)); or previously diagnosed type 2 diabetes.

"Impaired insulin sensitivity" is a disorder in which one or more of the body's normal physiological responses to insulin are impaired or lost. Impaired insulin sensitivity in a subject is characterized by a reduced biological response to endogenous or exogenous insulin. Impaired insulin sensitivity is associated with a number of diseases or disorders in humans, including increased risk of developing type 2 diabetes. Impaired insulin sensitivity is also a feature of metabolic syndrome, which is a cluster of abnormalities that create risk for many of our most common medial diseases or disorders. Impaired insulin sensitivity can be determined by methods such as the oral glucose tolerance test (OGTT), IV glucose tolerance test (FSIVGTT), insulin tolerance test (ITT), insulin sensitivity test (1ST), and continuous infusion of glucose with model assessment (CIGMA), or the glucose clamp. See, e.g., Krentz, Insulin Resistance (Wiley-Blackwell, 2002); de Paula Martins et al., Eur. J. Obst. Gynecol. Reprod. Biol., 133 (2):203-207. Obesity, Body Mass Index (BMI) and Visceral Adiposity.

"Diabetes" is a disorder generally characterized by metabolic defects in production and utilization of glucose that result in the failure to maintain appropriate blood sugar levels in the body. The result of these defects is elevated blood glucose, referred to as "hyperglycemia." Diabetes in humans can be defined as a disorder corresponding to a fasting plasma glucose concentration greater than 125 mg/dL, or a plasma glucose concentration greater than 199 mg/dL two hours after ingestion of a 75 g oral glucose load. Two major forms of diabetes are type 1 diabetes and type 2 diabetes. Type 1 diabetes is generally the result of an absolute deficiency of insulin, the hormone that regulates glucose utilization. Type 2 diabetes often occurs in the face of normal, or even elevated levels of insulin and can result from the inability of tissues to respond appropriately to insulin. Most Type 2 diabetic patients are insulin resistant (i.e., having impaired insulin sensitivity) and have a relative deficiency of insulin, in that insulin secretion cannot compensate for the resistance of peripheral tissues to respond to insulin. In addition, many type 2 diabetics are obese. Type 1.5 diabetes (late autoimmune onset in adults) shows some characteristics of type 1 and type 2 diabetes.

"Glucose tolerance" refers to a state of proper functioning of the homeostatic mechanisms by which insulin is secreted in response to an elevation in blood glucose concentrations. Impairment in this system results in transient hyperglycemia as the organism is unable to maintain normoglycemia following a glucose load (for example, a carbohydrate containing meal) because of insufficient secretion of insulin from the islet beta-cells or because of insensitivity of target tissues to circulating insulin. "Impaired glucose tolerance" in humans can be defined as a plasma glucose concentration greater than or equal to 140 mg/dl (7.8 mmol/l) two hours after ingestion of a 75 g oral glucose load.

DETAILED DESCRIPTION

I. General

The invention provides monoclonal antibody 3H6 and related antibodies, such as antibodies that bind to an epitope within residues 28-36 of IAPP. The antibodies of the invention are useful, for example, for treating disorders associated with IAPP accumulation, particularly accumulation of IAPP deposits. Such disorders include type 2 diabetes, metabolic syndrome, impaired insulin tolerance, impaired glucose tolerance, insulinomas, and related conditions.

II. IAPP

Unless otherwise apparent from the context, reference to IAPP means human islet-amyloid polypeptide, which is a 37 amino acid peptide having the sequence:

(SEQ ID NO: 1)
KCNTATCATQRLANFLVHSSNNFGAILSSTNVGSNTY.

IAPP is originally synthesized as residues 34-70 of an 89-amino acid precursor protein (Swiss Prot P10997) of which residues 1-22 are a signal peptide, and residues 23-31 and 74-89 are propeptides. Mature IAPP can form "oligomers", which are soluble multimeric assemblies of two or more IAPP peptides.

III. Antibodies

3H6 is an exemplary antibody of the invention, whose heavy and light chain mature variable regions are designated SEQ ID NO: 9 and SEQ ID NO: 20, respectively. The invention also provides antibodies competing with 3H6 for binding to IAPP, or which bind to the same or overlapping epitope as an antibody designated 3H6 and have similar functional properties, such as stabilizing blood glucose levels and thereby reducing, ameliorating or preventing impaired glucose tolerance.

Other antibodies having such binding specificity can be produced by immunizing mice with IAPP or a fragment thereof (i.e., a fragment including amino acid residues 27-37, or a portion thereof, such as amino acid residues 28-36), and screening the resulting antibodies for binding to IAPP, optionally in competition with 3H6. Antibodies can also be screened for their effect (1) in IAPP transgenic rodent models subjected to oral glucose challenge or other test, (2) on rodent or other non-human animal model for a disease characterized by IAPP accumulation by oral glucose challenge or other test, and/or (3) in humans with a condition associated with IAPP accumulation by oral glucose challenge or other test. Alternatively, or in addition to any of the foregoing approaches, antibodies can be screened against mutagenized forms of IAPP to identify an antibody showing the same or similar binding profile as 3H6 to a collection of mutational changes. The mutations can be systematic substitution with alanine (or serine if an alanine is present already) one residue at a time, or more broadly spaced intervals, throughout IAPP or through a section thereof in which the epitope is known to reside (e.g., residues 27-37 or 28-36).

Antibodies having the binding specificity of a selected murine antibody (e.g., 3H6) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for IAPP (e.g., at least $10^8$ $M^{-1}$, and preferably at least $10^9$ $M^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for IAPP are selected. The resulting antibodies usually have the same or similar epitope specificity as the murine starting material.

Other antibodies can be obtained by mutagenesis of cDNA encoding the heavy and light chains of an exemplary antibody, such as 3H6. Accordingly, monoclonal antibodies that are at least 70%, 80%, 90%, 95%, 96%, 97%, 98% or 99% identical to 3H6 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention.

The invention also includes monoclonal antibodies having at least 3, 4, 5 and preferably all six CDR(s) as defined by Kabat that are 90%, 95%, 99% or 100% identical to corresponding CDRs of 3H6. Such monoclonal antibodies preferably have at least 70%, 80%, 90%, 95%, 96%, 97%, 98% or 99% identity to 3H6 in amino acid sequence of the mature heavy and/or light chain variable regions and maintain its functional properties, and/or differ from 3H6 by a small number of functionally inconsequential amino acid substitutions (e.g., conservative substitutions), deletions, or insertions.

Preferred antibodies show similar functional activity to 3H6, e.g., in stabilizing blood glucose levels and/or hemoglobin A1c in a human with or at risk of any condition associated with IAPP accumulation disclosed herein or in an animal model thereof. As used herein, a level of blood glucose or hemoglobin A1c is considered "stabilized" if, when measured under specific conditions, the level in a subject with a condition associated with IAPP accumulation does not increase (beyond experimental error) over time or, increases at a lower rate than in an untreated control subject over the same period of time. Thus, stabilization of blood glucose levels can be shown when, under conditions such as fasting or following an oral glucose challenge, one or more measurements of blood glucose in an afflicted subject (e.g., human subject) treated with an anti-IAPP antibody of the invention (e.g., for a period of at least 18 weeks) is not higher (beyond experimental error) than corresponding prior measurement(s) of blood glucose in the afflicted subject (e.g., prior to treatment), or at least one or more measurements of blood glucose in the afflicted subject is lower than corresponding measurement(s) of blood glucose in an afflicted control subject (e.g., a subject that has received, over the same period of time, a control antibody, a placebo, or no treatment at all). Similarly, stabilization of hemoglobin A1c levels can be shown when a measurement of hemoglobin 1Ac in an afflicted subject (e.g., human subject) treated with an anti-IAPP antibody of the invention (e.g., for a period of at least 18 weeks) is not greater (beyond experimental error) than a corresponding prior measurement of hemoglobin 1Ac in the afflicted subject (e.g., prior to treatment), or the measurement of hemoglobin 1Ac in the afflicted subject is lower than a corresponding measurement of hemoglobin 1Ac in an afflicted control subject (e.g., a subject that has received, over the same period of time, a control antibody, a placebo, or no treatment at all).

Preferably, treatment with an anti-IAPP antibody of the invention is for a sufficient period of time (e.g., for 5, 10, 15, 18, 20, 22, 24, 26, 28, 30, or more weeks) such that, after a 120 minute oral glucose challenge, the afflicted subject's blood glucose level is the same as (within experimental error) or less than a prior corresponding measurement of blood glucose (e.g., an oral glucose challenge measurement taken earlier in the treatment or prior to the start of treatment) in the same subject. Preferably, treatment with an anti-IAPP antibody of the invention (e.g., for 5, 10, 15, 18, 20, 22, 24, 26, 28, 30, or more weeks) stabilizes the blood glucose levels of an afflicted subject such that, at one or more time points after an oral glucose challenge (e.g., 30', 60', 90', 120', 150', and/or 180'), the afflicted subject's blood glucose levels are the same as (within experimental error) or less than prior corresponding measurements of blood glucose in the same subject.

Preferably, treatment with an anti-IAPP antibody of the invention if for a sufficient period of time (e.g., for 5, 10, 15, 18, 20, 22, 24, 26, 28, 30, or more weeks) such that, after a 120 minute oral glucose challenge, the afflicted subject's blood glucose level is less than a corresponding measurement of blood glucose in an afflicted control subject. Preferably, treatment with an anti-IAPP antibody of the invention (e.g., for 5, 10, 15, 18, 20, 22, 24, 26, 28, 30, or more weeks) stabilizes the blood glucose levels of an afflicted subject such that, at one or more time points after an oral glucose challenge (e.g., 30', 60', 90', 120', 150', and/or 180'), the afflicted subject's blood glucose levels are less than corresponding measurements of blood glucose in an afflicted control subject.

Preferably, treatment with an anti-IAPP antibody of the invention (e.g., for 5, 10, 15, 18, 20, 22, 24, 26, 28, 30, or more weeks) stabilizes the hemoglobin A1c level of an afflicted subject such that the afflicted subject's hemoglobin A1c level is the same as (within experimental error) or less than a prior measurement of hemoglobin A1c in the same subject (e.g., a measurement taken earlier in the treatment or prior to the start of treatment). Preferably, treatment with an anti-IAPP antibody of the invention (e.g., for 5, 10, 15, 18, 20, 22, 24, 26, 28, 30, or more weeks) stabilizes the hemoglobin A1c level of an afflicted subject such that the afflicted subject's hemoglobin A1c level is less than the corresponding measurement of blood glucose in an afflicted control subject.

Stabilization preferably occurs while a subject is receiving a recurring treatment regime and continues for at least 3, 6, or 12 months, or indefinitely.

Exemplary methods of measuring stabilization of blood glucose levels and reduction in hemoglobin A1c in the rat HIP model are provided in the Examples that follow. Blood glucose levels and hemoglobin A1c levels can be measured, e.g., in whole blood, serum, or plasma. Regardless of the method, the difference between blood glucose levels or hemoglobin A1c levels in an afflicted treated subject and an afflicted control subject, under the specified conditions, should be statistically significant or otherwise beyond experimental error.

A. Chimeric and Veneered Antibodies

The invention further provides chimeric and veneered forms of non-human antibodies, particularly 3H6.

A chimeric antibody is an antibody in which the mature variable regions of light and heavy chains of a non-human antibody (e.g., a mouse) are combined with light and heavy chain constant regions from an antibody of a different species. Typically, the light and heavy chain constant regions are of human origin, but the constant regions can originate from a different non-human species, such as a rat, as needed (e.g., to facilitate testing of the non-human antibody in an appropriate animal model). Such antibodies substantially or entirely retain the binding specificity of the non-human (e.g., mouse) antibody supplying the variable regions, and are about two-thirds human (or different non-human species) sequence.

A veneered antibody is a type of humanized antibody that retains some and usually all of the CDRs and some of the non-human variable region framework residues of a nonhuman antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more humanlike by the substitutions. Veneered forms of 3H6 are included in the invention.

B. Humanized Antibodies

A humanized antibody is a genetically engineered antibody in which the CDRs from a non-human "donor" antibody (e.g., 3H6) are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly, a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. And a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and Dabs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85%, 90%, 95%, or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs) from a mouse antibody. See, e.g., Pascalis et al. (20020, J. Immunol. 169:3076; Vajdos et al. (2002), Journal of Molecular Biology, 320: 415-428; Iwahashi et al. (1999), Mol. Immunol. 36:1079-1091; and Tamura et al. (2000), Journal of Immunology, 164:1432-1441.

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al. (2004), Mol. Immunol. 41: 863. For such humanized antibodies, at positions in which one or more donor CDR residues are absent or in which an entire donor CDR is omitted, the amino acid occupying the position can be an amino acid occupying the corresponding position (by Kabat numbering) in the acceptor antibody sequence. The number of substitutions of acceptor for donor amino acids in the CDRs that can be included reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65%-85% identity) between the human acceptor sequence variable region frameworks and corresponding variable region frameworks of the donor antibody chain.

Certain amino acids from the human variable region framework residues can be selected for substitution (i.e., backmutation) based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 Å of a CDR region), (e.g., identified by modeling the light or heavy chain on the solved structure of a homologous known immunoglobulin chain); and
(4) a residue participating in the VL-VH interface.

Framework residues from classes (1)-(3) as defined by Queen (U.S. Pat. No. 5,530,101) can be alternately referred to as canonical or vernier residues. Framework residues that help determine the conformation of a CDR loop are sometimes referred to as canonical residues (Chothia and Lesk, J. Mol. Biol. 196, 901-917 (1987), Thornton & Martin *J. Mol. Biol.*, 263, 800-815, 1996). Framework residues that support antigen-binding loop conformations and play a role in fine-tuning the fit of an antibody to antigen are sometimes referred to as vernier residues (Foote & Winter, 1992, *J Mol Bio.* 224, 487-499).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

The invention provides humanized forms of the mouse 3H6 antibody. The mouse antibody comprises mature heavy and light chain variable regions having amino acid sequences comprising SEQ ID NO: 9 and SEQ ID NO: 20, respectively. The invention provides three exemplified humanized mature heavy chain variable regions (H1, SEQ ID NO: 14; H2, SEQ ID NO: 15; and H3, SEQ ID NO: 16) and four exemplified humanized mature light chain variable region (L1, SEQ ID NO: 25; L2, SEQ ID NO: 26; L3, SEQ ID NO: 27; and L4, SEQ ID NO: 28). The H1L1 variant, which includes five backmutations, provides an affinity to IAPP that is about 20 nM, which is substantially the same as the murine 3H6 antibody within experimental error. The H2L1 and H3L2 variants, which each include three backmutations, provide an affinity to IAPP that is between 30 nM and 35 nM.

The invention provides variants of the H1L1 humanized 3H6 antibody in which the humanized mature heavy chain variable region shows at least 90%, 95%, 96%, 97%, 98%, or 99% identity to H1 (SEQ ID NO: 14) and the humanized mature light chain variable region shows at least 90%, 95%, 96%, 97%, 98%, or 99% sequence identity to L1 (SEQ ID NO: 25). In some such antibodies, one, two, three, four or five of the backmutations in H1L1 are retained. In some antibodies, position H78 in the Vh region is occupied by V and/or position H94 in the Vh region is occupied by I. In some antibodies, at least 1, 2, or 3 of positions L36, L45, and L86 in the Vk region is/are occupied by L, K, and H, respectively. Some antibodies have positions L36, L45 and L86 in the Vk region are occupied by L, K and H, respectively, some of which additionally have positions H78 and H94 in the Vh region occupied by V and I, respectively, for example, the H2L1 and H1L1 variants. Some antibodies have positions H94, L36 and L45 occupied by I, L and K, respectively, for example, the H3L2 variant. The CDR regions of such humanized antibodies can be identical or substantially identical to the CDR regions of H1L1, which are the same as those of the mouse donor antibody. The CDR regions can be defined by any conventional definition (e.g., Chothia) but are preferably as defined by Kabat.

One possibility for additional variation in humanized 3H6 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution or even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutation. For example, when using a heavy chain acceptor sequence in which position H78 is already occupied by V, no backmutation is necessary.

The invention also includes humanized antibodies in which the mature light and heavy chain variable regions shows at least 90, 95, 96, 97, 98 or 99% sequence identity to the mature light and heavy chain variable regions of the humanized 3H6 H1L2, H1L3, H1L4, H2L1, H2L2, H2L3, H2L4, H3L1, H3L2, H3L3, or H3L4.

C. Selection of Constant Region

The heavy and light chain variable regions of chimeric, humanized (including veneered), or human antibodies can be linked to at least a portion of a constant region sufficient to interact with an Fc receptor. The constant region is typically human, but a non-human (e.g., rat) constant region can be selected as needed.

The choice of constant region depends, in part, on whether antibody-dependent complement and/or cellular mediated cytotoxicity is desired. For example, human isotopes IgG1 and IgG3 have complement-mediated cytotoxicity whereas human isotypes IgG2 and IgG4 have poor or no complement-mediated cytotoxicity. A human IgG1 constant region suitable for inclusion in the antibodies of the invention can have the sequence of SEQ ID NO: 34. Light chain constant regions can be lambda or kappa. A human kappa light chain constant region suitable for inclusion in the antibodies of the invention can have the sequence of SEQ ID NO: 36. Another human kappa light chain constant region suitable for inclusion in the antibodies of the invention can have the sequence of SEQ ID NO: 72, which differs from SEQ ID NO: 36 in that it has the addition of an N-terminal arginine. Antibodies can be expressed as tetramers containing two light and two heavy chains, as separate heavy chains, as separate light chains, as Fab, Fab', F(ab')$_2$, or Fv fragments, or as single chain antibodies in which heavy and light chain variable regions are linked through a spacer.

Human constant regions show allotypic variation and isoallotypic variation between different individuals. That is, the constant regions can differ in different individuals at one or more polymorphic positions. Isoallotypes differ from allotypes in that sera recognizing an isoallotype binds to a non-polymorphic region of one or more other isotypes. Thus, for example, another heavy chain constant region is of the IgG1 G1m3 allotype and has the amino acid sequence of SEQ ID NO: 69. Another heavy chain constant region of the IgG1 G1m3 allotype has the amino acid sequence of SEQ ID NO: 70. Reference to a human constant region includes a constant region with any natural allotype or any permutation of residues occupying polymorphic positions in natural allotypes or up to 3, 5 or 10 substitutions for reducing or increasing effector function as described below.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduces affinity for Fcγ receptors, particularly FcγRI receptor (see, e.g., U.S. Pat. No. 6,624,821). An alanine substitution at positions 234, 235 and 237 of human IgG1 can be used for reducing effector functions. Optionally, positions 234, 236 and/or 237 in human IgG2 are substituted with alanine and position 235 with glutamine. (See, e.g., U.S. Pat. No. 5,624,821.). In some aspects, a mutation at one or more of positions 241, 264, 265, 270, 296, 297, 322, 329, and 331 by EU numbering of human IgG1 is used. In some aspects, a mutation at one or more of 318, 320, and 322 by EU numbering of human IgG1 is used. In some aspects, positions 234 and/or 235 are substituted with alanine and/or position 329 is substituted with glycine. In some aspects, positions 234 and 235 are substituted with alanine, such as in SEQ ID NO: 70. In some aspects, the isotype is human IgG2 or IgG4.

D. Human Antibodies

Human antibodies against IAPP are provided by a variety of techniques described below. Some human antibodies are selected by competitive binding experiments, or otherwise, to have the same or overlapping epitope specificity as 3H6. Human antibodies can also be screened for a particular epitope specificity by using only a fragment of IAPP (e.g., amino acid residues 27-37 or 28-36) as the immunogen, and/or by screening antibodies against a collection of deletion mutants of IAPP. One technique for producing human antibodies is trioma methodology (Oestberg et al., Hybridoma 2:361-367 (1983); Oestberg, U.S. Pat. No. 4,634,664; and Engleman et al., U.S. Pat. No. 4,634,666). Another technique involves immunizing transgenic mice expressing human immunoglobulin genes, such as the Xeno-Mouse®, AlivaMab Mouse or Veloceimmune mouse (see, e.g., Lonberg et al., WO93/1222, U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, Nature 148, 1547-1553 (1994), Nature Biotechnology 14, 826 (1996), Kucherlapati, WO 91/10741. Another technique is phage display (see, e.g., Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332. In these methods, libraries of phage are produced in which members display different antibodies on their outer surfaces. Antibodies are usually displayed as Fv or Fab fragments. Phage displaying antibodies with a desired specificity are selected by affinity enrichment to an IAPP peptide or fragment thereof. Another technique is to sequence DNA from human B cells according to the general protocols outlined in Reddy et al., *Nat Biotechnol.* 2010 September; 28(9):965-9. Epub 2010 August 29; and US 20110053803, 20100099103, 20100291066, 20100035763, and 20100151471. Briefly, B cells can be obtained from a human suspected of having anti-IAPP antibodies, e.g., a human immunized with IAPP, fragments thereof, longer polypeptides containing IAPP or fragments thereof, or anti-idiotypic antibodies. The mRNA of the antibodies from B cells is then reverse transcribed into cDNA and sequenced using, e.g., 454 sequencing technology. After obtaining the sequences of the chains from each antibody, the chains can be paired together (e.g., using bioinformatics), cloned, expressed, and screened for desired properties.

E. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to VH region leader peptide encompassing the translation initiation codon as the 5' primer and a g2b constant regions specific 3' primer. Exemplary primers are described in U.S. patent publication US 2005/0009150 by Schenk et al. (hereinafter, "Schenk"). The sequences from multiple, independently-derived clones, can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner as the VH region. In one approach, a consensus primer set designed for amplification of VL regions is designed to hybridize to the VL region encompassing the translation initiation codon, and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions. Exemplary sequences encoding human constant regions include SEQ ID NO: 33, which encodes a human IgG1 constant region, and SEQ ID NO: 35, which encodes a human kappa light chain constant region. Other exemplary sequences encoding human constant regions include SEQ ID NO: 68, which encodes a human IgG1 constant region of the G1m3 allotype, and SEQ ID NO: 71, which encodes a human kappa light chain constant region.

In one approach, the heavy and light chain variable regions are re-engineered to encode splice donor sequences downstream of the respective VDJ or VJ junctions, and cloned into the mammalian expression vector, such as pCMV-hγ1 for the heavy chain, and pCMV-Mc1 for the light chain. These vectors encode human γ1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hrs. post-transfection and assayed by western blot analysis for antibody production or ELISA for antigen binding. The chimeric antibodies are humanized as described above.

Chimeric, veneered, humanized, and human antibodies are typically produced by recombinant expression. Recombinant nucleic acid constructs typically include an expression control sequence operably linked to the coding sequences of antibody chains, including naturally associated or heterologous expression control element(s), such as a promoter. Once the vector has been incorporated into the appropriate host, the host is maintained under conditions suitable for high level expression of the nucleotide sequences, and the collection and purification of the cross reacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host useful for cloning the DNA sequences encoding the polypeptides disclosed herein. Microbes, such as yeast are also useful for expression. *Saccharomyces* is a yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a host cell for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed, and include CHO cell lines, various COS cell lines, HeLa cells, L cells, human embryonic kidney cell, and myeloma cell lines. The cells can be nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., J. Immunol. 148:1149 (1992).

Alternatively, antibody coding sequences can be incorporated in transgenes for introduction into the genome of a transgenic animal and subsequent expression in the milk of the transgenic animal (see, e.g., U.S. Pat. No. 5,741,957, U.S. Pat. No. 5,304,489, U.S. Pat. No. 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes, or can be incorporated into the genome of embryonic stem cells, and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, Protein Purification (Springer-Verlag, NY, 1982)).

Methodology for commercial production of antibodies can be employed, including codon optimization, selection of promoters, transcription elements, and terminators, serum-free single cell cloning, cell banking, use of selection markers for amplification of copy number, CHO terminator, serum free single cell cloning, improvement of protein titers (see, e.g., U.S. Pat. No. 5,786,464, U.S. Pat. No. 6,114,148, U.S. Pat. No. 6,063,598, U.S. Pat. No. 7,569,339, WO2004/050884, WO2008/012142, WO2008/012142, WO2005/019442, WO2008/107388, and WO2009/027471, and U.S. Pat. No. 5,888,809).

F. Antibody Screening Assays

Antibodies can be subject to several screens including binding assays, functional screens, screens in animal models of diseases associated with IAPP deposits, and clinical trials. Binding assays test for specific binding and, optionally, affinity and epitope specificity to IAPP (or a fragment thereof, such as amino acid residues 27-37 or 28-36). Such screens are sometimes performed in competition with an exemplary antibody such as 3H6. Optionally, either the antibody or IAPP target is immobilized in such assay. Functional assays can be performed in cellular models including cells naturally expressing IAPP or transfected with DNA encoding IAPP or a fragment thereof. Suitable cells include cells derived from pancreatic islet cells. Cells can be screened for reduced levels of IAPP (e.g., by Western blotting or immunoprecipitation of cell extracts or supernatants) or reduced toxicity attributable to IAPP.

Animal model screens test the ability of the antibody to therapeutically or prophylactically treat signs or symptoms in an animal model simulating a human disease associated with IAPP deposits, such as type II diabetes or impaired glucose tolerance. Suitable signs or symptoms that can be monitored include elevated blood glucose levels (e.g., fasting blood glucose levels or blood glucose levels following an oral glucose challenge) and/or elevated hemoglobin 1Ac levels. The extent of elevation can be determined by comparison with an appropriate control, such as blood glucose levels in control animals that have received a control antibody (e.g., an isotype matched control antibody), a placebo, or no treatment at all. Transgenic or other animal models of type 2 diabetes include HIP rats, db/db mouse, Zucker diabetic fatty rat, ob/ob mouse, high calorie-fed Psammomys obesus (sand rat), Goto-Katazaki rat (GK rat), and RIPHAT transgenic mice. Transgenic animals can include a human IAPP transgene. To facilitate testing in animal models, antibodies having a constant region appropriate for the animal model can be used (e.g., mouse-rat chimeric antibodies could be used for testing in HIP rats). It can be concluded that a humanized version of an antibody will be effective if the corresponding mouse antibody or chimeric antibody is effective in an appropriate animal model and the humanized antibody has similar binding affinity (e.g., by a factor of 1.5, 2, or 3, within experimental error).

Clinical trials test for safety and efficacy in a human having a disease associated with IAPP deposits.

IV. Pharmaceutical Compositions and Methods of Use

Provided herein are several methods of diagnosing, monitoring, treating or effecting prophylaxis of diseases or conditions associated with IAPP deposition (e.g., IAPP accumulation) or toxic IAPP oligomers. Examples of such diseases include Type 2 diabetes and related conditions, including metabolic syndrome, impaired insulin sensitivity, impaired glucose tolerance, or insulinomas. Antibodies described above can be incorporated into pharmaceutical composition for use in such methods. In general, an antibody or pharmaceutical composition containing an antibody is administered to a subject in need thereof. Patients amenable to treatment include individuals at risk of an IAPP associated disease but not showing symptoms, as well as patients presently showing symptoms. Therefore, the pharmaceutical compositions can be administered prophylactically to individuals who have a known genetic risk of an IAPP-associated disease. Such individuals include those having relatives who have experienced such a disease, and those whose risk is determined by analysis of genetic or biochemical markers, including the diagnostic methods provided herein. See, e.g., Janssens et al. (2006), Predictive genetic testing for type-2 diabetes, *BMJ*, 333:509-510; Saxena et al., (2010), *Nat Gen*, 42:142-148. Besides family history and genetics, low activity level, poor diet, and excess body weight (especially around the waist) significantly increase the risk of developing type 2 diabetes. Other risk factors include: an age greater than 45 years; an HDL cholesterol of less than 35 mg/dL or triglyceride level of greater than 250 mg/dL; high blood pressure; history of gestational diabetes; previously identified impaired glucose tolerance; and race/ethnicity (African Americans, Hispanic Americans, and Native Americans all have high rates of diabetes). Though often no symptoms are shown, individuals suffering from T2D can sometimes be recognized from its clinical manifestations including high blood glucose levels, blurred vision, erectile dysfunction, fatigue, frequent or slow-healing infections, increased appetite, increased thirst, increased urination. As warranted by family history, genetic testing or medical screening for type-2 diabetes, treatment can begin at any age (e.g., 10, 20, 30). Usually, however, it is not necessary to begin treatment until a patient reaches 40, 50, 60 or 70. Treatment typically entails multiple dosages over a period of time and can be monitored by assaying antibody or activated T-cell or B-cell responses to a therapeutic agent (e.g., a truncated form of IAPP) over time. If the response falls, a booster dosage is indicated.

The identification of the subject can occur in a clinical setting, or elsewhere, e.g., in the subject's home, e.g., through the subject's own use of a self-testing kit. For example, the subject can be identified based on various symptoms such as increased thirst, increased frequency of urination, increased hunger, weight loss, fatigue, blurred vision, slow-healing sores, frequent infections, and areas of darkened skin. In some examples, the subject can be identified using a fasting blood glucose level test (e.g., testing to see if glucose is 100-125 mg/dL after an overnight or eight hour fast) or an oral glucose tolerance test (e.g., testing to see if glucose levels are 140-199 mg/dL two hours after taking a dose of a high-sugar solution). In humans, fasting levels less than 100 mg/dL or oral glucose tolerance test levels less than 140 mg/dL are considered normal, levels of 100-125 (fasting) or 140-199 (oral glucose tolerances test) are considered impaired (pre-diabetic) and levels of >125 (fasting) or >199 (oral glucose tolerance test) are considered not only impaired but diabetic. In prophylactic applications, an antibody or a pharmaceutical composition of the same is administered to a subject susceptible to, or otherwise at risk of a disease (e.g., a Type 2 diabetes disease) in a regime (dose, frequency and route of administration) effective to reduce the risk, lessen the severity, or delay the onset of at least one sign or symptom of the disease. In therapeutic applications, an antibody or immunogen to induce an antibody is administered to a subject suspected of, or already suffering from a disease (e.g., a Type 2 diabetes disease) in a regime (dose, frequency and route of administration) effective to ameliorate or at least inhibit further deterioration of at least one sign or symptom of the disease.

A regime is considered therapeutically or prophylactically effective if an individual treated subject achieves an outcome more favorable than the mean outcome in a control population of comparable subjects not treated by methods disclosed herein, or if a more favorable outcome is demonstrated for a regime in treated subjects versus control subjects in a controlled clinical trial (e.g., a phase II, phase II/III, or phase III trial) or an animal model at the p<0.05 or 0.01 or even 0.001 level.

An effective regime of an antibody can be used for, e.g., reducing islet amyloid polypeptide (IAPP) accumulation in a subject having or at risk of a condition associated with IAPP accumulation; inhibiting aggregation of islet amyloid polypeptide (IAPP) in a subject having or at risk of a condition associated with IAPP accumulation; inhibiting toxic effects of IAPP oligomers in a subject having or at risk of a condition associated with toxic IAPP oligomers or IAPP accumulation; stabilizing a non-toxic conformation of islet amyloid polypeptide (IAPP) in a subject having or at risk of a condition associated with toxic conformations of IAPP or IAPP accumulation; reducing islet amyloid polypeptide deposits (IAPP) in a subject having or at risk of developing IAPP deposits; clearing aggregated islet amyloid polypeptide in a subject having or at risk of a condition associated with IAPP accumulation; stabilizing or reducing glucose levels in a subject having Type 1 Diabetes (T1D); stabilizing or reducing glucose levels in a subject having Type 1.5 Diabetes (T1.5D); stabilizing or reducing glucose levels in a subject having Type 2 Diabetes (T2D); reducing beta islet cellular toxicity associated with aggregates or oligomers of IAPP in a subject having or at risk of a condition associated with toxic conformations of IAPP or IAPP accumulation; reducing, ameliorating, or preventing impaired glucose tolerance in a subject having or at risk of a condition associated with toxic conformations of IAPP or IAPP accumulation; ameliorating impaired fasting glucose in a subject having or at risk of a condition associated with toxic conformations of IAPP or IAPP accumulation; treating or effecting prophylaxis of a condition associated with amyloid accumulation in a subject (e.g., a condition (e.g., T2D, metabolic syndrome, glucose intolerance, insulinomas or inflammation) associated with amyloid accumulation in the pancreas of the subject); reducing inflammation in a subject associated with amyloid accumulation in the subject, e.g., accumulation in the subject's pancreas; diagnosing the presence or absence of an amyloid accumulation in a pancreas by contacting a sample suspected of comprising the amyloid accumulation with an effective amount of an agent that binds to an epitope within the N-terminal region of IAPP; determining a level of IAPP deposits in a subject by detecting the presence of bound antibody in the subject following administration of the agent; inducing an immune response comprising antibodies to IAPP in a subject; delaying the onset of a condition associated with amyloid accumulation in a subject; preventing or delaying progression of pre-diabetes to diabetes in a subject with impaired fasting glucose (for example, having a fasting blood glucose level of 100 to 125 milligrams per deciliter after an overnight fast), impaired glucose tolerance (for example, having a blood glucose level of 140 to 199 milligrams per deciliter after a 2-hour oral glucose tolerance test) or both IFG and IGT; methods of stabilizing fasting blood glucose levels in a subject at less than 100 milligrams per deciliter after an overnight fast; and/or methods of stabilizing blood glucose levels in a subject at less than 140 milligrams per deciliter after a 2-hour oral glucose tolerance test.

Effective doses vary depending on many different factors, such as means of administration, target site, physiological state of the subject, and whether the subject is human or an animal, other medications administered, and whether treatment is prophylactic or therapeutic.

An exemplary dose range for antibodies can be from about 0.01 to 10 mg/kg, and more usually 0.1 to 3 mg/kg or 0.15-2 mg/kg or 0.15-1.5 mg/kg, of subject body weight. Antibody can be administered in such doses daily, on alternative days, weekly, fortnightly, monthly, quarterly, or according to any other schedule determined by empirical analysis. An exemplary treatment entails administration in multiple doses over a prolonged period, for example, of at least six months. Additional exemplary treatment regimes entail administration once per every two weeks or once a month or once every 3 to 6 months.

Antibodies can be administered via a peripheral route (i.e., one in which an administered or induced antibody crosses the blood brain barrier to reach an intended site in the brain. Routes of administration include topical, intravenous, oral, subcutaneous, intraarterial, intracranial, intrathecal, intraperitoneal, intranasal or intramuscular. Routes for administration of antibodies can be intravenous or subcutaneous. This type of injection is most typically performed in the arm or leg muscles. In some methods, agents are injected directly into a particular tissue where deposits have accumulated, for example intracranial injection.

Pharmaceutical compositions for parenteral administration can be sterile and substantially isotonic and manufactured under GMP conditions. Pharmaceutical compositions can be provided in unit dose form (i.e., the dose for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, e.g., in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The regimes can be administered in combination with another agent effective in treatment or prophylaxis of the disease being treated.

After treatment, the subject's condition can be evaluated to determine the progress or efficacy of such treatment. Such methods preferably test for stabilization in blood glucose levels. Such levels can be measured after a subject has fasted (e.g., for 8-16 hours)). Alternatively, or in addition, the test can evaluate the blood glucose levels of a subject at a specified period (e.g., 2 hrs.) after ingestion of a specified quantity of glucose, e.g., 75 g (referred to as in an oral glucose challenge test). The subject's blood glucose level may be evaluated to determine improvement (i.e., lower glucose level) relative to the subject's glucose level under comparable circumstances prior to treatment (i.e. fasting glucose level or glucose level after oral glucose challenge test). The subject's blood glucose level can also be compared with control populations under comparable circumstances. The control populations can be similarly afflicted untreated subjects or normal untreated subjects (among other control subjects). Improvement (decreased levels) relative to similarly afflicted untreated subjects or levels approaching or reaching the levels in untreated normal subjects indicates a positive response to treatment. Methods of measuring blood glucose levels and related kits are well-known.

The extent to which glucose levels are being controlled can be determined indirectly by measuring glycated hemoglobin levels in the blood, for example, hemoglobin A1c or HbA1c levels. Other indirect measures of the extent to which glucose levels are being controlled include measuring blood insulin levels. Efficacy can also be monitored by assessing changes in IAPP amyloid levels by a number of methods, including imaging techniques. Examples of suitable imaging techniques include PET scanning with radiolabeled IAPP or fragments thereof, IAPP antibodies or fragments thereof, Congo red based amyloid imaging agents such as, for example, PiB (US 20110008255, amyloid-imaging peptide p31 (Biodistribution of amyloid-imaging peptide, p31, correlates with amyloid quantitation based on Congo red tissue staining, Wall et al., Abstract No. 1573, 2011 ISNM Annual Meeting) and other PET labels.

A. Diagnostics and Monitoring Methods

Also provided are methods of detecting an immune response against IAPP in a patient suffering from or susceptible to diseases associated with IAPP deposition or toxic IAPP oligomers. The methods can be used to monitor a course of therapeutic and prophylactic treatment with the agents provided herein. For example, the methods can be used to monitor active immunization (e.g., antibody produced in response to administration of immunogen) and passive immunization (e.g., measuring level of administered antibody).

Also provided are methods of detecting IAPP amyloid in a subject, for example, by measuring IAPP amyloid in a sample from a subject or by in vivo imaging of IAPP in a subject. Such methods are useful to diagnose or confirm diagnosis of diseases associated with IAPP, or susceptibility thereto. The methods can also be used on asymptomatic subjects. The presence of abnormal deposits of IAPP indicates susceptibility to future symptomatic disease. The methods are also useful for monitoring disease progression and/or response to treatment in subjects who have been previously diagnosed with an IAPP-associated disease.

Fluid or tissue samples obtained from a subject having, suspected of having, or at risk of having an IAPP-associated disease can be contacted with the antibodies disclosed herein to assess the presence of IAPP amyloid. For example, levels of IAPP amyloid in such subjects may be compared to those present in healthy subjects. Alternatively, levels of IAPP amyloid in such subjects receiving treatment for the disease may be compared to those of subjects who have not been treated for an IAPP-associated disease. Some such tests involve a biopsy of tissue obtained from the pancreas of such subjects. ELISA assays may also be useful methods, for example, for assessing IAPP levels in fluid samples. Some such ELISA assays involve IAPP antibodies that preferentially bind oligomeric or aggregated forms of IAPP relative to monomeric forms of IAPP.

The in vivo imaging methods can work by administering a reagent, such as antibody that binds to IAPP in the subject, and then detecting the reagent after it has bound. Antibodies typically bind to an epitope of IAPP within the N-terminal region of IAPP. If desired, the clearing response can be avoided by using antibody fragments lacking a full length constant region, such as Fabs. In some methods, the same antibody can serve as both a treatment and diagnostic reagent.

Diagnostic reagents can be administered by intravenous injection into the body of the subject, or via other routes deemed reasonable. The dose of reagent should be within the same ranges as for treatment methods. Typically, the reagent is labeled, although in some methods, the primary reagent with affinity for IAPP is unlabeled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled loci to corresponding base line values. The base line values can represent the mean levels in a population of undiseased individuals. Base line values can also represent previous levels determined in the same subject. For example, base line values can be determined in a subject before beginning treatment, and measured values thereafter compared with the base line values. A decrease in values relative to base line generally signals a positive response to treatment.

B. Passive Immunization

The antibody profile following passive immunization typically shows an immediate peak in antibody concentration followed by an exponential decay. Without a further dose, the decay approaches pretreatment levels within a period of days to months depending on the half-life of the antibody administered. For example the half-life of some human antibodies is of the order of 20 days.

In some methods, a baseline measurement of antibody to IAPP in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dose of antibody is administered. In some methods, peak or subsequent measured levels less background are compared with reference levels previously determined to constitute a beneficial prophylactic or therapeutic treatment regime in other subjects. If the measured antibody level is significantly less than a reference level (e.g., less than the mean minus one or, preferably, two standard deviations of the reference value in a population of subjects benefiting from treatment) administration of an additional dose of antibody is indicated.

V. Kits

Also provided are kits including an IAPP-specific antibody and instructions for use. Such kits can be used for, e.g., performing the diagnostic methods described above. A kit can also include a label. Kits also typically contain labeling providing directions for use of the kit. The labeling may also include a chart or other correspondence regime correlating levels of measured label with levels of antibodies to IAPP. The term labeling generally refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Also provided are diagnostic kits for performing in vivo imaging. Such kits typically contain an antibody binding to an epitope of IAPP as described herein. The antibody can be labeled or a secondary labeling reagent is included in the kit. The kit can include instructions for performing an in vivo imaging assay.

EXAMPLES

Example 1: Assessment of IAPP Fragments and Full-Length IAPP in Male HIP Rats

This example describes administration of IAPP peptides to transgenic rats. The HIP rat is a transgenic rodent model which incorporates a gene that encodes the human form of Islet Amyloid PolyPeptide (IAPP) and results in overproduction of this peptide. Butler et al. (2004), Diabetes Vol. 53:1509-16. IAPP is a normally produced peptide which is co-secreted with insulin by the pancreatic islet cells. When secreted at pathological levels, IAPP can self-associate, leading to amyloid deposition.

EL-IAPP/fragments and EL-IAPP/intact are peptides, which, when coupled with keyhole limpet hemocyanin, serve as immunogens that lead to the formation of anti-IAPP antibodies that are being investigated for their potential to block diabetes caused by IAPP-induced islet cell toxicity.

This study was designed to look at the effects of dosing EL-IAPP/fragments and EL-IAPP/intact in the male HIP rat.

Materials and Methods

Test Articles

Test articles (TAs) were solutions/suspensions containing conjugates of EL-IAPP/fragments and EL-IAPP/intact with keyhole limpet hemocyanin (KLH) in phosphate buffered saline (PBS). EL-IAPP/fragments contained CKKG-GAILSSTNVGSN-amide (SEQ ID NO: 2), which includes human IAPP amino acid residues 24-35, and C-LSSTNVG-SNTY (SEQ ID NO: 3), which includes hIAPP amino acid residues 27-37, coupled to KLH via a maleimide linker to the cysteines. EL-IAPP/intact was full-length IAPP coupled via glutaraldehyde cross linking to KLH.

Dose Formulations

Formulation in Complete Freunds Adjuvant:

Complete Freunds Adjuvant (CFA) is an oil-based formulation containing 10 mg *Mycobacterium tuberculosis* per 10 mL as an immunostimulant. To formulate doses for intraperitoneal (ip) injections an emulsion was prepared, with the test articles being delivered in the aqueous phase.

Equal volumes of CFA and PBS were measured by volume and vortexed for approximately 1 minute prior to being sonicated using a Branson 450 sonicator fitted with a micro tip. The power settings were at 50% with an output level of 3. The micro tip was placed at 3 different levels in the formulation and pulsed for 3-5 pulses at each level. The formulation became thick, foamy and white (except where the original aqueous phase was colored). The formulation was considered complete when one drop of formulation was dripped into distilled water and it held its shape. The formulation was then drawn up into a syringe using an 18G needle which was replaced by a 22G needle for dosing. Dose volumes were set at 0.5 mL/animal.

For formulations which contained either EL-IAPP/fragments or EL-IAPP/intact, the correct volume of test article was calculated based on supplying 150 µg of test article per dose volume of 0.5 mL/animal. The volume of the immunogen needed was diluted to the total volume of the aqueous phase with PBS prior to mixing with equal parts of CFA as described.

Formulation in Incomplete Freunds Adjuvant:

Incomplete Freunds Adjuvant lacks the *Mycobacterium tuberculosis* of the Complete Freunds Adjuvant. Formulations of TAs in IFA were completed in a similar manner as described for CFA except that IFA was used instead of CFA, with no deleterious effect on the formulation. As with CFA, for doses that contained the test articles, the appropriate volume was used to deliver 150 µg of test article per dose volume of 0.5 mL/animal and was incorporated as the aqueous phase, being diluted to the total aqueous phase volume with PBS prior to mixing with equal volumes of IFA. After homogenization the doses were drawn up into syringes for delivery.

Formulation in PBS

For the final dose of the immunization schedule, the test articles were delivered as a dilute solution in PBS. The appropriate volume of the test article was calculated and diluted with PBS to deliver a final concentration of 150 µg of TA per dose volume of 0.5 mL/animal.

Dose Preparation

Doses were prepared freshly according to the immunization schedule shown in Table 1, below.

TABLE 1

| Group Frequency | TA | Dose 1 Week 1 | Dose 2 Week 3 | Dose 3 Week 5 | Dose 4 Week 9 | Dose 5 Week 13 | Dose 6 Week 17 | Dose 7 Week 21 | Dose 8 Week 25 |
|---|---|---|---|---|---|---|---|---|---|
| 1 (n = 25) | VC | CFA | IFA | IFA | IFA | IFA | IFA | IFA | PBS |
| 2 (n = 25) | TA2 | CFA | IFA | IFA | IFA | IFA | IFA | IFA | PBS |
| 3 (n = 25) | TA1 | CFA | IFA | IFA | IFA | IFA | IFA | IFA | PBS |
| 4 (n = 25) | C | — | | | | | | | |

Terms:
TA—test article;
VC—vehicle control;
TA1—C-terminal fragments of IAPP;
TA2—full-length IAPP;
C—study control (no dosing);
CFA—Complete Freunds Adjuvant;
IFA—Incomplete Freunds Adjuvant;
PBS—phosphate buffered saline.

Test System
  Receipt, Selection, and Disposition
  Male HIPP rats were bred by Charles River from a breeding colony. Animals (100 total, 25 per group) were selected based on availability, weight, and age, and were randomly assigned to groups.
  Justification for Test System and Number of Animals
  The HIPP rat is a genetically engineered model designed to mimic human type 2 diabetes disease. Immunization of the rats against formation of IAPP oligomers/deposits, which destroy insulin secretory cells, would prevent or slow the onset of diabetes.
  Each group was sized to be able to observe changes in blood glucose, weight, and antibody formation while allowing correlations to be made with sufficient numbers of animals to observe trends and differentiate between treatments.
  With both a vehicle control and a study control, in which the animals were not dosed, the effects of the emulsion of CFA and IFA could be identified to assist in study interpretation.
  Justification for Dose Level Selection
  Doses of 150 μg of protein (TA1 or TA2) via ip injection were considered adequate to elicit a response, while minimizing possible toxicity.
  Clinical Observations
  Clinical observations were performed twice daily to assess for signs of morbidity, mortality, and test compound toxicity. General signs of ill health were assessed, such as not eating, changes in weight, coat condition, and changes in behavior.
  Body Weights
  Body weights were recorded before initial treatment and twice weekly thereafter to assess weight loss as a criterion for euthanasia.
Sample Collection
  Blood
  Samples of blood were taken from the tail vein, following an overnight fast seven days post-immunization, for assessment of blood glucose levels and antibody titer. Rats were placed in an appropriate sized restrainer with the tail exposed. The tail was wiped with an alcohol wipe to clean the surface of the tail and help visualize the lateral veins. A butterfly catheter was inserted into one of the lateral veins and blood exiting the catheter was collected into a serum micro-container tube for antibody analysis after processing to serum. After removal of the catheter, a single drop of blood was collected onto a glucose test strip, which was then placed into a Freestyle lite (Abbott) glucometer and glucose values were read. The rats were removed from the restrainer after bleeding had ceased and returned to their cages.
Results
  Treating censored times-to-becoming-diabetic (i.e., time until blood glucose level goes higher than 300 mg/dl) as actual event times, the average time to becoming diabetic in animals receiving the full length IAPP (36.56 weeks) was slightly higher than the other three groups, with 34.64 weeks, 35.6 weeks, and 34.8 weeks for the untouched study control (Group 4), adjuvant control (Group 1), and C-terminal fragments of IAPP injected animals (Group 3), respectively. For the effect of C-terminal fragments of IAPP (Group 3), the time to becoming diabetic was not statistically different from that of the Group 4 study control (p=0.9836, 2-sided). In fact, immunization with C-terminal fragments of IAPP did not result in titer over 1000, which is thought to be the minimal level required for a protective effect. For the effect of full length IAPP (Group 2), a borderline significant protective effect (p=0.0540, 1-sided) was observed as compared to the study control group (Group 4). For the effect of adjuvant alone, no difference was detected between Group 1 and the Group 4 study control (p-value=0.4189, 2-sided).

Example 2: Isolation of Murine 3H6

LA28-3H6 was originally a mouse hybridoma, producing an anti-hIAPP antibody of isotype Gamma 2a k, which resulted from a fusion of spleen cells from a mouse injected with hIAPP coupled to KLH via gluteraldehyde. The mouse was immunized with 25 μg of the conjugate in RIBI adjuvant on days 0, 7, 14, 21, 39, 46, 53, 60, 77, 84, and 91. A serum sample was taken on day 70 and the titer of the mouse was found to be 44K against human IAPP. On day 97 the mouse was injected with the IAPP/KLH conjugate both intraperitoneally and intravenously. Three days later the spleen was removed and a cell suspension was generated and frozen. Four months later the suspension was thawed and fused to SP2/0 cells. The fusion was screened against hIAPP, then epitope mapped against shorter peptides and found to react with LSSTNVGSNTY (SEQ ID NO: 4), which corresponds to amino acids 27-37 of IAPP.

Example 3: Effects of Antibody 3H6 in HIP Rats after 18-22 Weeks of Treatment

To test that ability of the 3H6 antibody to alleviate abnormal glucose metabolism, such as associated with type 2 diabetes, the rat HIP model was selected. To facilitate such testing, chimeric mouse-rat 3H6 antibodies were generated.

Mouse-Rat 3H6 Chimeric Antibodies

Briefly, the PS/2 rat hybridoma was purchased from ATCC. As per information provided by ATCC, the PS/2 hybridoma expresses an IgG2b/kappa isotype rat antibody. mRNA was purified from PS/2 cells using QiagenOligotex Direct mRNA kit. Purified mRNA was then directly used for PCR amplification of the constant regions using Invitrogen SuperScript III One-Step RT-PCR Platinum kit. Rat constant regions were amplified using IgG2b and kappa specific forward and reverse primers. PCR fragments were purified and subcloned into a plasmid for sequencing. DNA sequencing verified that the cloned sequences correspond to the rat IgG2b and kappa constant regions. The rat heavy and light chain constant regions were then subcloned into pCET expression vectors downstream from the mouse 3H6 variable heavy chain and light chain regions, respectively. These resulting vectors were expressed in CHO cells to produce mouse-rat 3H6 chimeric antibodies.

Administration of Chimeric 3H6 Antibodies to HIP Rats

Animals.

50 male rats, strain CD(SD) HIP, 10-12 weeks of age, were used in the study.

Food and Water.

HIP rats were fed standard irradiated rodent chow ad libitum except during fasting; filtered drinking water was provided ad libitum.

Fasting.

Fasting of the HIP rats occurred every two weeks for assessment of fasting blood glucose levels. Food was removed 16-18 hours prior to the test and returned upon completion of the test.

Test Compound Preparation.

The test compounds consisted of mouse-rat chimeric 3H6 and PS2 antibodies (an isotype control). The test compounds were supplied as a sterile solution below 1 eu/mg endotoxin, and usually below <0.1 eu/mg endotoxin. The test compounds were formulated at pH 7.4 in 8 mM sodium phosphate, 2 mM potassium phosphate, 0.14M sodium chloride, and 10 mM potassium chloride.

Experimental Methodology.

HIP rats were divided into groups of 25 animals. Each group received test articles as shown in Table 2. The rats received weekly injections of the specified test articles, at 2 mL/kg (5 mg/mL) provided as a sterile solution. Injections were performed intraperitoneally (ip).

TABLE 2

Group Assignments

| Group | Strain | N | Test article designation | Dose mg/Kg | Dose Volume Max. | Route | Necropsy |
|---|---|---|---|---|---|---|---|
| 1 | HIP | 25 | 3H6 | 10 | 2 ml/kg | ip | Necropsy Day 1 |
| 3 | HIP | 25 | PS2 | 10 | 2 ml/kg | ip | Necropsy Day 3 |

Body Weights.

Individual animal weights were determined twice weekly throughout the course of this study beginning with baseline weights on or prior to study day −7. As body weight is linked to the disease/phenotype being studied, a change in body weight was not automatically considered as an indicator of toxicity.

Glucose Screening.

Fasting glucose measurements were recorded every two weeks for each animal throughout the study via a handheld glucometer. Food was withheld the previous night and returned after blood has been taken via the tail vein. A pre-study glucose screen was conducted on or prior to Study day −7.

Sample Collections.

A sample of blood, not exceeding 0.5 mL, was taken via the tail vein every two weeks, processed to serum and shipped to Elan, and frozen at −70 C. A pre-study blood sample was drawn at Study Day −7 to establish baseline antibody level.

Fasting Blood Glucose and Oral Glucose Tolerance Test

After 18 weeks of treatment, as described above and in particular in Table 2, HIP rats were fasted for 16 hours. After fasting, at a time designated "time 0", the fasting blood glucose value was determined for each rat in the study, via a hand held glucose meter. The fasting blood glucose level of HIP rats treated with 3H6 antibody was, on average, lower than the fasting blood glucose level of HIP rats that received the PS2 isotype control antibody, but the difference was not statistically significant. See FIG. 1B.

Figure 1B:
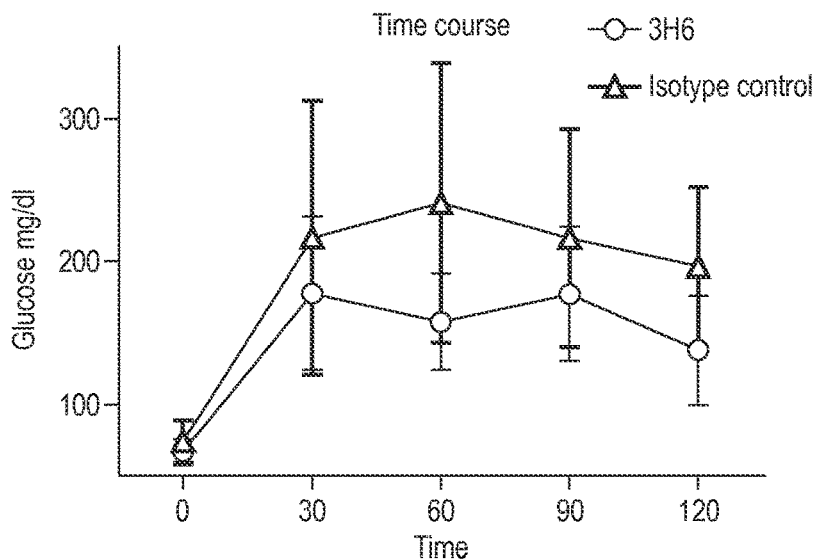
FIG. 1B is a graph of the results of the glucose challenge test. The graph shows the average blood glucose levels in the HIP rats just prior to the oral glucose challenge (time 0) and 30, 60, 90, and 120 minutes after ingestion of glucose. The error bars in FIGS. 1A and 1B represent one standard deviation from the mean.

The oral glucose tolerance test can be more sensitive than fasting blood glucose levels for detecting pre-diabetes and is considered the gold standard in diagnosis. Accordingly, following detection of fasting blood glucose levels, the HIP rats were dosed via gavage at 2 g/kg glucose. Blood samples were then collected at 30, 60, 90, and 120 minutes after dosage, and blood glucose levels were detected. As shown in FIG. 1B, the average blood glucose level of HIP rats that received the 3H6 antibody was significantly lower at 60 and 120 minutes post-glucose administration, as compared to the average blood glucose level of HIP rats that received the PS2 isotype control antibody. See FIG. 1A (significance was determined using the Mann Whitney test). In addition, at 30 and 90 minutes into the oral glucose tolerance test, the average blood glucose levels of HIP rats treated with the 3H6 antibody trended lower and had narrower standard deviations than the average blood glucose levels of HIP rats that received the PS2 isotype control antibody. A graph of the change in average blood glucose levels over the course of the oral glucose tolerance test is shown in FIG. 1B. The standard time point for screening for glucose impairment is at 120 minutes.

Another test for abnormal glucose metabolism involves the detection of hemoglobin A1c in the blood. Hemoglobin A1c (HbA1c) was first recognized by Rahbar as an abnormal hemoglobin associated with diabetes in 1969. The abnormality was later identified as chemical glycation of the N-terminal lysine and valines of hemoglobin A. The chemical reaction includes an initial, reversible, formation of the aldehyde Schiff base, followed by essentially irreversible Amadori rearrangement to the stable ketoamine. See Saudek & Brick (2009), "The clinical use of hemoglobin A1c." J Diabetes Sci Technol 3(4): 629-634.

Figure 2:
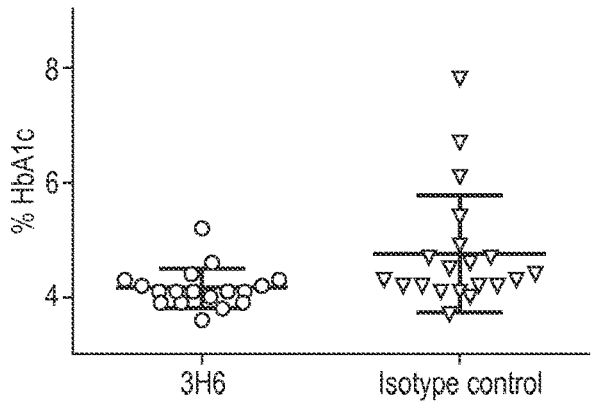
FIG. 2 depicts hemoglobin 1Ac levels in the blood of the HIP rats after twenty-two weeks of treatment with either 3H6 antibody or PS2 isotype control antibody.

Hemoglobin A1c levels in HIP rats was measured at Charles River labs, using an ACE Alera Analyzer, after 22 weeks of treatment with test articles according to Table 2, above. As shown in FIG. 2, HIP rats that had received the 3H6 antibody showed significant difference in hemoglobin A1c levels as compared to rats that had received the PS2 isotype control antibody (P=0.0069).

Example 4: Effects of Antibody 3H6 in HIP Rats after 24 Weeks of Treatment

Figure 3A:
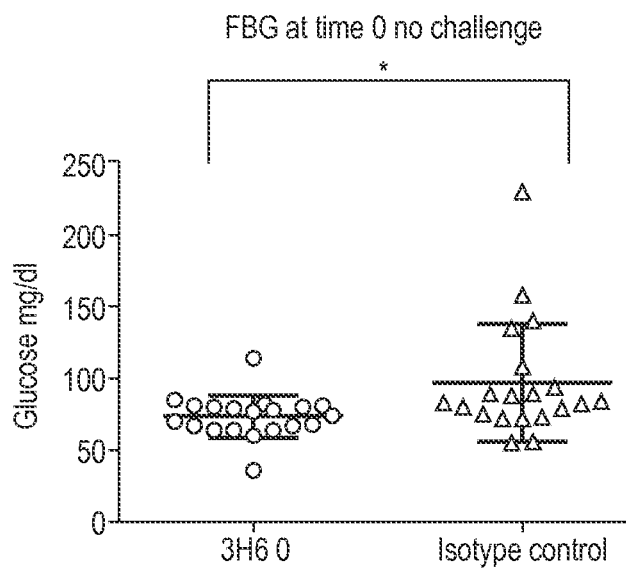
FIG. 3A depicts fasting blood glucose (FBG) levels in the HIP rats following twenty-four (24) weeks of treatment with either 3H6 antibody or a PS2 isotype control antibody.
Figure 3B:
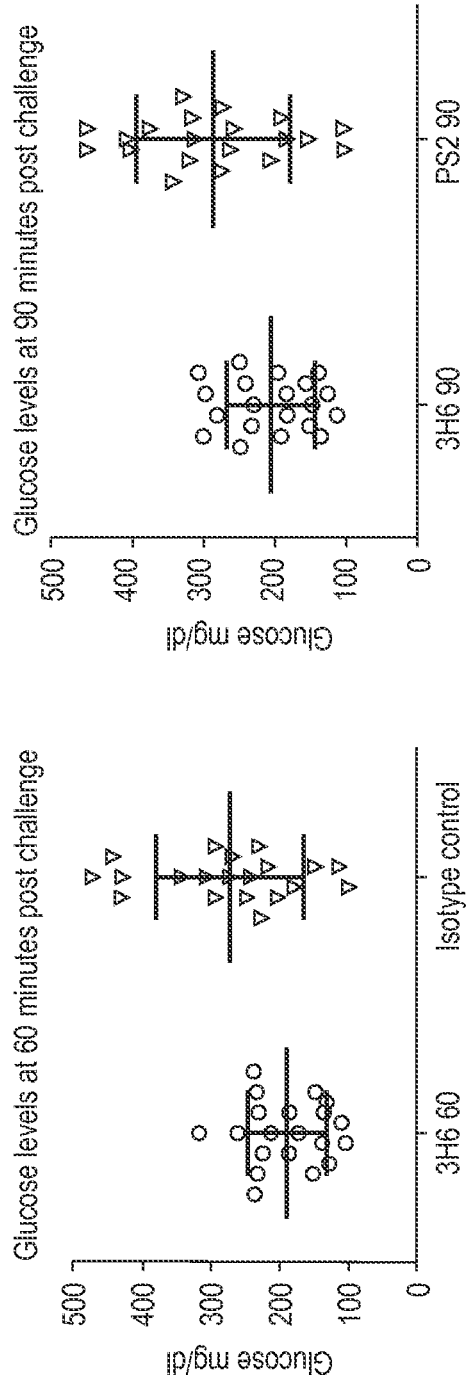
FIG. 3B depicts the blood glucose levels of the HIP rats during an oral glucose challenge test in which 2 g/kg of glucose was ingested after an overnight fast. The individual panels show the blood glucose levels measured at 60, 90, 120, and 180 minutes after administration of glucose.
Figure 3B:
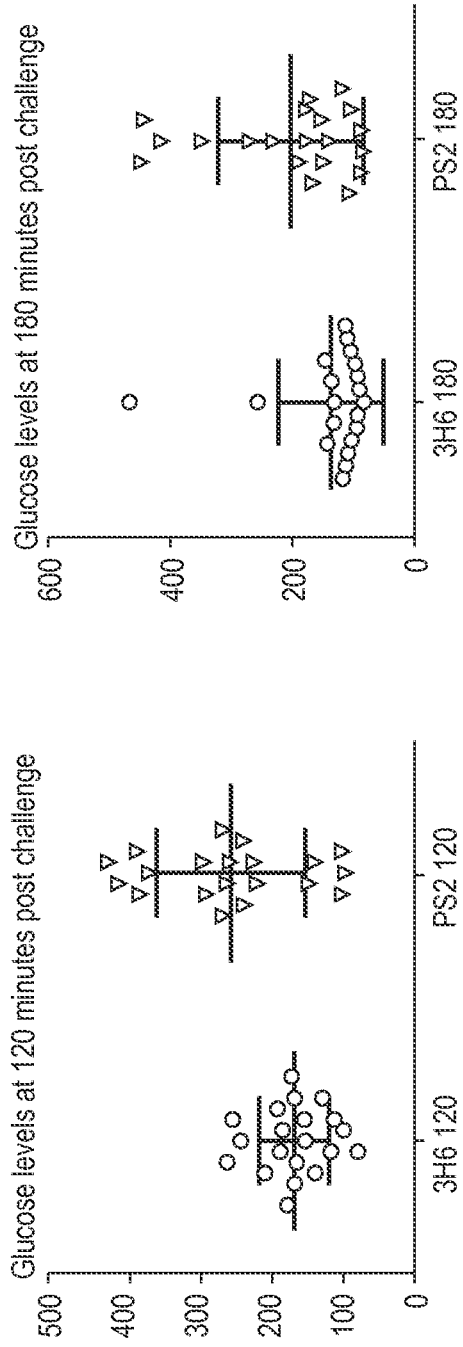
Figure 3C:
FIG. 3C is a graph of the results of the glucose challenge test. The graph shows the average blood glucose levels just prior to the oral glucose challenge (time 0) and 30, 60, 90, 120, and 180 minutes after ingestion of glucose. The error bars in FIGS. 3A-3C represent one standard deviation from the mean.

After 24 weeks of treatment, the 3H6-treated and PS2 isotype control-treated HIP rats of Example 3 were again submitted to an oral glucose tolerance test, with blood glucose levels determined prior to glucose administration and at 30, 60, 90, 120, and 180 minutes into the test. The average fasting blood glucose level of HIP rats treated with the 3H6 antibody was significantly lower (p=0.0101) than the average fasting blood glucose level of HIP rats that received the PS2 isotype control antibody. See FIG. 3A. Average blood glucose levels were also significantly lower in rats that were treated with the 3H6 antibody at 60, 90, 120, and 180 minutes into the oral glucose tolerance test. See FIG. 3B. A graph of the average blood glucose levels of HIP rats over the course of the oral glucose tolerance test is shown in FIG. 3C.

Example 5: Effects of Antibody 3H6 in HIP Rats after 28 Weeks of Treatment

Figure 4A:
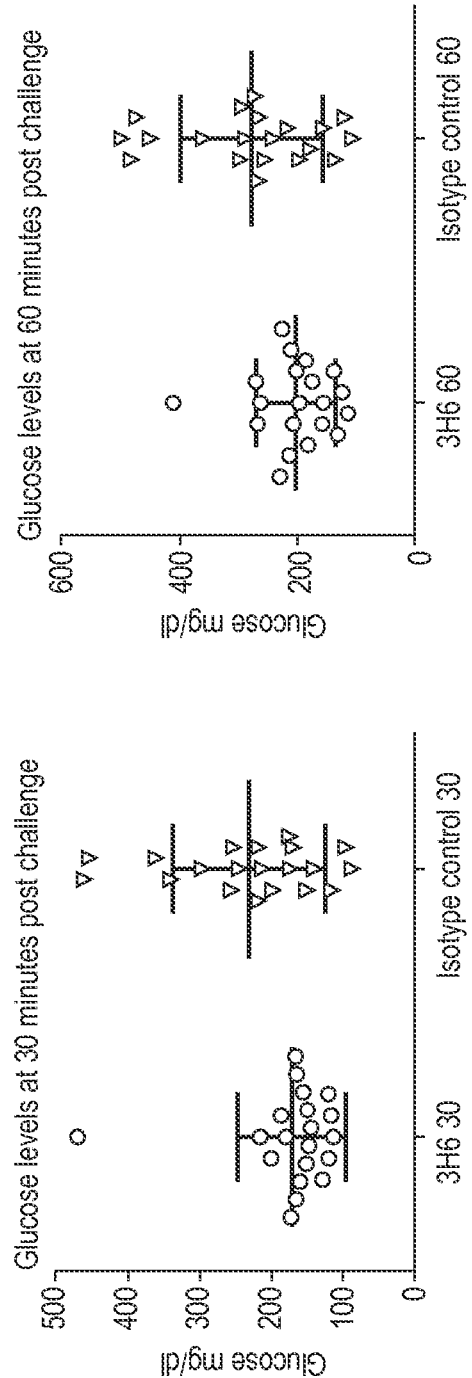
FIG. 4A depicts the blood glucose levels in the HIP rats after twenty-eight (28) weeks of treatment with either 3H6 antibody or PS2 isotype control antibody. The blood glucose levels were measured as part of an oral glucose challenge test in which 2 g/kg of glucose was ingested after an overnight fast. The individual panels show the blood glucose levels measured at 30, 60, 90, 120, and 180 minutes after administration of glucose.
Figure 4A:
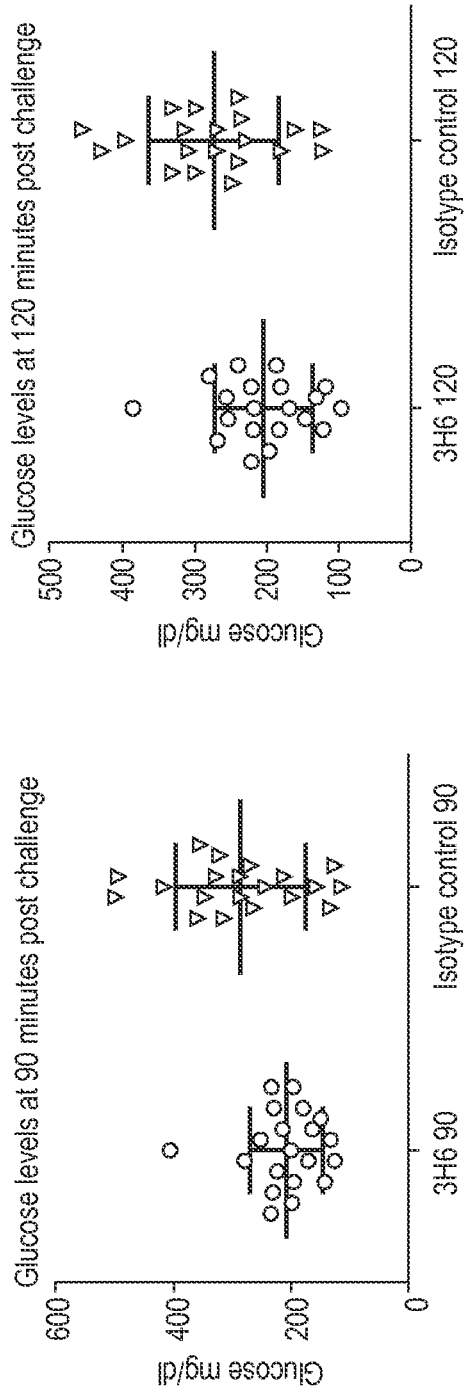
Figure 4A:
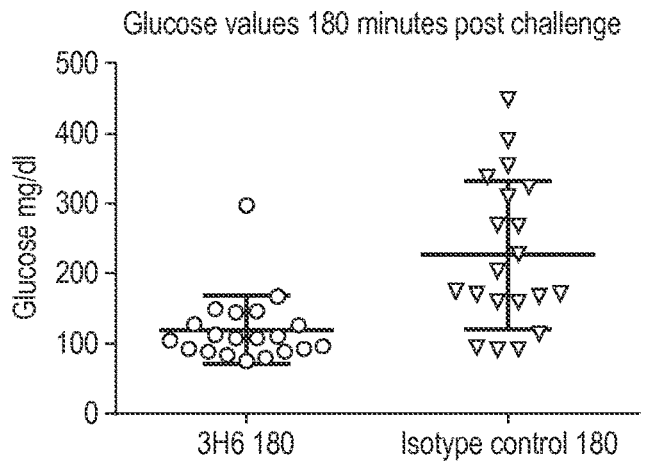
Figure 4B:
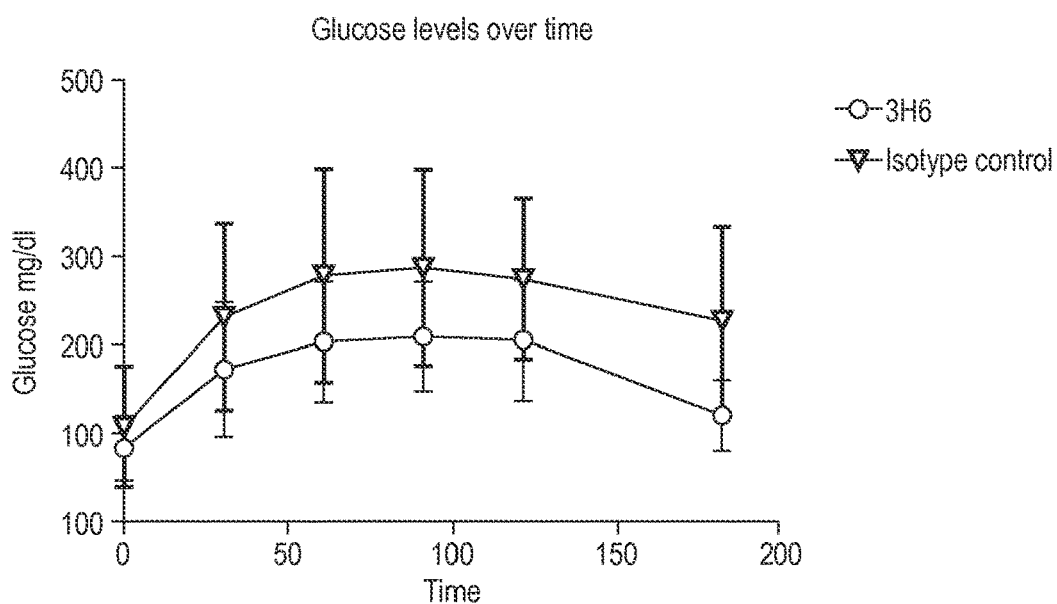
FIG. 4B is a graph of the results of the glucose challenge test. The graph shows the average blood glucose levels just prior to the oral glucose challenge (time 0) and 30, 60, 90, 120, and 180 minutes after ingestion of glucose. The error bars in FIGS. 4A and 4B represent one standard deviation from the mean.

After 28 weeks of treatment, the 3H6-treated and PS2 isotype control-treated HIP rats of Examples 3 and 4 were submitted to another oral glucose tolerance test, with blood glucose levels determined prior to glucose administration and at 30, 60, 90, 120, and 180 minutes into the test. The fasting blood glucose level of HIP rats treated with 3H6 antibody was, on average, lower than the fasting blood glucose level of HIP rats that received the PS2 isotype control antibody, though the difference was not statistically significant. See FIG. 4B. However, at all subsequent time points during the oral glucose tolerance test, a significant reduction in average blood glucose levels of HIP rats treated with the 3H6 antibody, as compared to the PS2 isotype control antibody, was observed. See FIG. 4A. A graph of the average blood glucose levels of HIP rats over the course of the oral glucose tolerance test is shown in FIG. 4B.

Taken together, the blood glucose data obtained from HIP rats at 18, 24, and 28 weeks shows that the 3H6 antibody affects multiple parameters implicated as indicators of the development of Type 2 diabetes, including Hemoglobin A1c levels, which increase based on the amount of time an animal has heighten circulating glucose levels. The 3H6 antibody also significantly helps maintain homeostasis of glucose levels after the animal is orally challenged with glucose.

Example 6: Humanization of 3H6

RNA was extracted from pelleted cells expressing the 3H6 antibody. The resulting RNA was reverse transcribed to produce cDNA, and nucleic acid sequences coding for the immunoglobulin heavy chain and light chain variable regions of the 3H6 antibody were amplified by PCR. The PCR products were gel purified, cloned, and sequenced.

Nucleic acid encoding the 3H6 heavy chain variable region has the sequence of SEQ ID NO:5. The corresponding protein sequence, which includes a signal peptide at positions 1-19 (underlined) is as follows:

(SEQ ID NO: 6)
MDLRLSCAFIIVLLKGVQSEVKLEESGGGLVQPGGSMKLSCVASGFTFS

NYWMYWVRQSPEKGLEWVAEIRLKSDNYATHYAESVKGRFTISRDDSKS

SVYLQMNSLRAEDTGIYYCTIFDYWGQGTTLVTVSS

Nucleic acid encoding the 3H6 light chain variable region has the sequence of SEQ ID NO:7. The corresponding protein sequence, which includes a signal peptide at positions 1-19 (underlined) is as follows:

(SEQ ID NO: 8)
MSPAQFLFLLVLWIRETNGDVVMTQTPLTLSVTIGQPASISCKSSQSLL

DSDGKTYLNWLLQRPGQSPKRLIYLVSKLDSGVPDRFTGSGSGTDFTLK

ISRVEAEDLGVHYCWQGRHFPYTFGGGTKLEIK

The amino acid sequence for the mature 3H6 heavy chain variable region (SEQ ID NO: 9) is shown in FIGS. 6A-E, and the corresponding amino acid sequence for the mature 3H6 light chain variable region (SEQ ID NO: 20) is shown in FIGS. 7A-E. Kabat numbering is used throughout.

The 3H6 light chain variable region is a variable kappa (Vk) region that belongs to mouse Kabat subgroup 2, which corresponds to human Kabat subgroup 3. The 3H6 heavy chain variable region belongs to mouse Kabat subgroup 3, which corresponds to human Kabat subgroup 3C. See Kabat et al. (1991) Sequences of Proteins of Immunological Interest, Fifth Edition. NIH Publication No. 91-3242.

Analysis of the CDRs of the 3H6 Vk region reveals a 16 residue CDR-L1 (SEQ ID NO: 21) belonging to canonical class 4, a 7 residue CDR-L2 (SEQ ID NO: 22) belonging to canonical class 1, and a 9 residue CDR-L3 (SEQ ID NO: 23) belonging to canonical class 1. See Martin & Thornton (1996), Structural families in loops of homologous proteins: automatic classification, modeling and application to antibodies. J Mol Biol. 263:800-15. Similar analysis of the CDRs of the 3H6 Vh region reveals a 5 residue CDR-H1 (SEQ ID NO: 10) belonging to canonical class 1, and a 19 residue CDR-H2 (SEQ ID NO: 11) belonging to canonical class 3. See Martin & Thornton (1996), supra. The 3H6 Vh region also includes a 3 residue CDR-H3 (SEQ ID NO: 12) that does not belong to any canonical class.

Analysis of the residues at the interface between the 3H6 Vk and Vh regions reveals that most of the residues are the ones commonly found, with the exceptions of l93 in the heavy chain (usually an alanine) and L36 in the light chain (typically tyrosine or phenylalanine). These irregular residues are prime targets for backmutation.

A search was made over the protein sequences in the PDB database to identify structures that could provide a rough model of 3H6. See Deshpande et al. (2005), The RCSB Protein Data Bank: a redesigned query system and relational database based on the mmCIF schema, Nucleic Acids Res. 33:D233-7. The crystal structure of dimeric antibody 17.2 (pdb code 3SGE; Pizarro et al. (2001), Structural and functional characterization of a monoclonal antibody specific for the preS1 region of hepatitis B virus, FEBS Lett. 509:463-8) was settled upon for the Vk structure since it has good resolution (1.89 A) and overall sequence similarity to 3H6 Vk, retaining the same canonical structures for the loops. Antibody 5F6 (pdb code 3NZH; Teplyakov et al. (2010), On the domain pairing in chimeric antibodies, Mol. Immunol. 47(14):2422-6) was settled upon for the Vh structure, as it also has good overall sequence similarity and reasonably good resolution (2.0 A). In addition, CDR-H1 and CDR-H2 of the 5F6 antibody have the same canonical structures as the corresponding CDRs in 3H6 Vh. Bioluminate software was used to model a rough structure of 3H6.

A search of the non-redundant protein sequence database from NCBI allowed selection of suitable human frameworks into which to graft the 3H6 murine CDRs. For Vk, a human kappa light chain with NCBI accession code 523230 (GI: 284256; SEQ ID NO: 24) was chosen. See Kennedy et al. (1991), J. Exp. Med. 173 (4), 1033-1036. This human Vk region has the same canonical classes for CDR-L1 and CDR-L2 as the 3H6 Vk region. It is a member of Kabat human kappa subgroup 1. For Vh, human Ig heavy chain ABI74422.1 (GI:114386331; SEQ ID NO: 13) was chosen. Again, it has the same canonical classes for CDR-L1 and CDR-L2 as the 3H6 Vh region. It is a member of Kabat human heavy subgroup 3.

The humanized heavy and light chain variable region designs and backmutations based on the selected human frameworks are shown in FIGS. 6A-E and FIGS. 7A-E, respectively. Backmutations for humanized heavy chain variable region designs are listed in FIGS. 6A-E in the headers for columns 6, 7, and 8. Backmutations for humanized light chain variable region designs are listed in FIGS. 7A-E in the headers for columns 6, 7, 8, and 9.

Humanized Vh Region Designs

Three different humanized versions of the 3H6 Vh region were designed, H1, H2, and H3. For backmutations, vernier zone residues H78 and H94 were ultimately focused upon. In version 1 (H1, SEQ ID NO: 14), both positions are backmutated (to A78V and T94I), to preserve CDR packing. In version 2 (H2, SEQ ID NO: 15), the A78V & T94I backmutations are eliminated to test the impact on CDR packing. In version 3 (H3, SEQ ID NO: 16), the A78V backmutation is eliminated and the T94I backmutation is kept.

Exemplary nucleic acid sequences encoding humanized 3H6 H1, H2, and H3 are provided in SEQ ID NOs: 17, 18, and 19, respectively.

Humanized Vk Region Designs

Four different humanized versions of the 3H6 Vk region were designed, L1, L2, L3, and L4. For backmutations, residues L36, L45, and L86 were ultimately focused upon. L36 is an important interface residue that interacts with CDR-L1, CDR-L2, CDR-L3, and CDR-H3, and further interacts with interface residues in the Vh region. L45 is important because the K residue in the mouse framework sequence contacts CDR-L2 and, based on the model, it appears that an R residue will form a de-novo hydrogen bond with L56 (a Ser residue) and restrict L2 CDR flexibility. L86 is important because the H residue in the mouse framework sequence is positively charged and replacing it with a Y residue, a hydrophilic non-charged residue, could potentially adversely impact packing in the vicinity of the variable region in which it is located.

In version 1 (L1, SEQ ID NO: 25), all framework residues at positions L36, L45, and L86 are backmutated to F36L, R45K, and Y86H. In version 2 (L2, SEQ ID NO: 26), the framework residues at positions L36 and L45 are backmutated to F36L and R45K. In version 3 (L3, SEQ ID NO: 27), none of the framework residues at positions L36, L45, and L86 are backmutated. And in version 4 (L4, SEQ ID NO: 28), the framework residues at positions L45 and L86 are backmutated to R45K and Y86H.

Exemplary nucleic acid sequences encoding humanized 3H6 L1, L2, L3, and L4 are provided in SEQ ID NOs: 29, 30, 31, and 32, respectively.

Example 7: IAPP-Binding Affinity of Humanized 3H6 Antibodies

The affinity of various combinations of 3H6 humanized heavy chains and humanized light chain proteins for IAPP was analyzed on a Biacore instrument. Biacore analysis was performed by preparing an anti-human CM5 chip following the protocol provided in the kit. The 3H6 antibody was captured such that the maximum binding of rat IAPP would not exceed 20-30 RU. Rat IAPP was used in the assays instead of human IAPP because the epitope recognized by the 3H6 antibody is identical in rat and human IAPP and rat IAPP does not aggregate in solution, allowing for cleaner kinetics measurements. Various concentrations of rat IAPP were flowed over the sensor for a time long enough that at least the higher concentrations resulted in equilibrium binding, and then allowed to dissociate from the chip for a length of time such that at least 10% of total bound IAPP had dissociated. Data was blank subtracted to both an irrelevant sensor not containing 3H6 and 0 IAPP concentration to account for the dissociation of 3H6 from the anti-human capture. Data was then analyzed using a global 1:1 fit.

As shown in Table 3, the H1L1 version of humanized 3H6 antibody has an affinity for human IAPP that is roughly equivalent to that of the mouse 3H6 antibody (KD=20.4 nM for H1L1 as compared to KD=18.6 for mouse 3H6), while the H2L1 and H3L2 versions have slightly lower, but still adequate affinities for IAPP.

TABLE 3

Affinity of 3H6 Humanized Antibody Versions for IAPP

| 3H6 variant | Mouse aa in Fwrk | | $K_D$ | $K_{on}$ | $K_{off}$ |
| --- | --- | --- | --- | --- | --- |
| | HC | LC | nM | 1/Ms | 1/s |
| m3H6 | 84Fwrk/30CDR | 80Fwrk/32CDR | 18.6 | 8.18E+04 | 0.00152 |
| ch3H6 | 84Fwrk/30CDR | 80Fwrk/32CDR | 13.7 | 10.74E+04 | 0.00147 |
| h3H6-H1L1 | A78V, T94I | F36L, R45K, Y86H | 20.4 | 11.32E+04 | 0.00231 |
| h3H6-H2L1 | None | F36L, R45K, Y86H | 34.5 | 8.52E+04 | 0.00294 |
| h3H6-H2L2 | None | F36L, R45K | 85.4 | 7.57E+04 | 0.00646 |
| h3H6-H3L2 | T94I | F36L, R45K | 33.2 | 18.81E+04 | 0.00625 |

Example 8: Epitope Mapping of 3H6 Antibody

To further identify the epitope of IAPP bound by the 3H6 antibody, 11 amino acid long biotinylated peptides, providing for a 1 amino acid walk of IAPP, were synthesized (by Mimetopes). Most of the peptides included an N-terminally biotinylated Ser-Gly-Ser-Gly linker at the N-terminal end. However, the N-terminal-most IAPP peptide (KCNTAT-CATQR, SEQ ID NO: 37) was C-terminally biotinylated instead of being N-terminally biotinylated. In addition, for the C-terminal-most IAPP peptide, versions were synthesized with either a free C-terminal amino acid (SEQ ID NO: 64) or an amidated C-terminal amino acid (SEQ ID NO: 63). The N-terminal-most and C-terminal-most peptides were designed to determine whether a neo-epitope (formed upon cleavage of the IAPP precursor protein) is needed for antibody binding.

For detection of binding between the hIAPP peptides and 3H6 antibody, the peptides were bound to a streptavidin-coated 96-well plate (PIERCED), then blocked with 1% bovine serum albumin (BSA) in phosphate buffered saline (PBS). Purified 3H6 antibody was diluted to 5 mg/ml in 1% BSA/PBS/0.1% Tween), then added to each well and incubated for 1 hour with the peptides. Following the incubation, wells were washed and horseradish peroxidase (HRP)-conjugated secondary antibody (goat anti-mouse) was added for another 1 hour incubation. The wells were washed again, then 3,3'5,5'-tetramethylbenzidine (TMB) was added for 5 minutes. Cleavage of TMB by HRP was stopped by addition of sulfuric acid, and the amount of TMB cleavage (which is proportional to the amount of 3H6 antibody bound to peptide in the same well) was detected spectraphotometrically.

Figure 5:
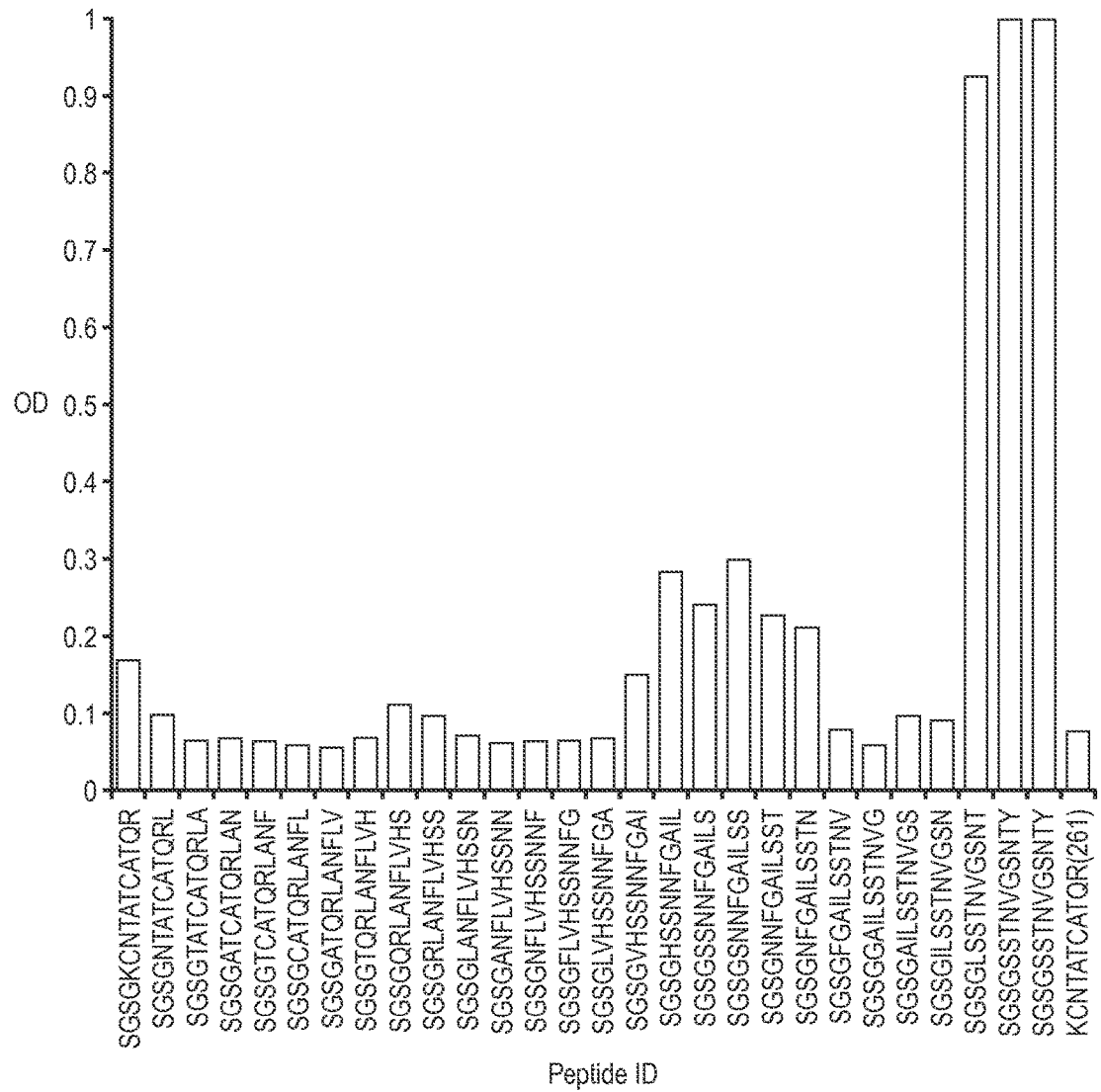
FIG. 5 is a bar graph depicting epitope mapping of murine 3H6 with respect to hIAPP. hIAPP peptides used in the experiment are shown on the X-axis, and correspond (from left to right) to SEQ ID NOS: 37 to 65. The peptides include: (i) a sequential series of 11 amino acid peptides from hIAPP, spanning the length of hIAPP in one amino acid increments, each fused to an N-terminally biotinylated Ser-Gly-Ser-Gly linker (SEQ ID NOS: 37 to 62 and SEQ ID NO: 64); (ii) a peptide containing an N-terminally biotinylated Ser-Gly-Ser-Gly linker fused to amino acid residues 27-37 of hIAPP, and further having an amidated C-terminal amino acid (SEQ ID NO: 63); and (iii) a peptide corresponding to amino acid residues 1-11 of hIAPP and having a biotinylated C-terminus (SEQ ID NO: 65). The size of the bars correlates with the extent of binding of 3H6 antibody to each of the peptides.

The resulting epitope map for 3H6 is shown in FIG. 5. The consensus epitope maps to the IAPP sequence SST-NVGSNT (SEQ ID NO: 67), which corresponds to amino acid residues 28-36.

Various changes in form and details can be made therein without departing from the spirit and scope of the invention. Unless otherwise apparent from the context, any embodiment, aspect, element, feature, step or the like can be used in combination with any other. Insofar as information associated with a citation may change with time, the information associated with the citation at the earliest effective filing date is meant, the earliest effective filing date for a citation meaning the filing date of the present application or earlier priority application disclosing the citation. All references, issued patents and patent applications cited within the body of the instant specification are hereby incorporated by reference in their entirety, for all purposes.

We claim:

1. An isolated monoclonal antibody that specifically binds to human IAPP comprising a mature heavy chain variable region comprising CDR1, CDR2 and CDR3 of SEQ ID NO: 14 and a mature light chain variable region comprising Kabat CDR1, CDR2 and CDR3 of SEQ ID NO: 25.

2. The antibody of claim 1 that is chimeric, veneered, or humanized.

3. The antibody of claim 1, wherein the antibody is a single-chain Fv antibody or a Fab fragment.

4. The antibody of claim 1, wherein the mature heavy chain variable region has an amino acid sequence at least 90% identical to H1 (SEQ ID NO: 14) and the mature light chain variable region has an amino acid sequence at least 90% identical to L1 (SEQ ID NO: 25).

5. The antibody of claim 4, comprising Kabat CDR1, CDR2 and CDR3 of SEQ ID NO: 14 and Kabat CDR1, CDR2 and CDR3 of SEQ ID NO: 20.

6. The antibody of claim 5, provided at least one of positions H1, H41, H78 and H94 is occupied by E, P, V and I, respectively, and at least one of positions L36, L45, and L86 is occupied by L, K, and H, respectively, wherein positions are defined by Kabat numbering.

7. The antibody of claim 6, provided positions H1, H41, H78 and H94 are occupied by E, P, V and I, respectively, and positions L36, L45, and L86 are occupied by L, K, and H, respectively.

8. The antibody of claim 6, provided positions H1 and H41 are occupied by E and P, respectively, and positions L36 and L45 are occupied by L and K, respectively, wherein positions are defined by Kabat numbering.

9. The antibody of claim 8, provided position H94 defined by Kabat numbering is occupied by I.

10. The antibody of claim 9, provided position H78 defined by Kabat numbering is occupied by V.

11. The antibody of claim 10, provided position L86 defined by Kabat numbering is occupied by H.

12. The antibody of claim 4, wherein the mature heavy chain variable region has an amino acid sequence at least 95% identical to H1 (SEQ ID NO: 14) and the mature light chain variable region has an amino acid sequence at least 95% identical to L1 (SEQ ID NO: 25).

13. The antibody of claim 4, wherein the mature heavy chain variable region is fused to a heavy chain constant region and the mature light chain variable region is fused to a light chain constant region.

14. The antibody of claim 13, wherein the mature heavy chain variable region is fused to a heavy chain constant region having the sequence of SEQ ID NO: 34 and/or the mature light chain variable region is fused to a light chain constant region having the sequence of SEQ ID NO: 36.

15. The antibody of 22 or 26, wherein the mature heavy chain variable region has an amino acid sequence designated H1 (SEQ ID NO: 14) and the mature light chain variable region has an amino acid sequence designated L1 (SEQ ID NO: 25).

16. The antibody of claim 4, wherein the mature heavy chain variable region has an amino acid sequence designated H2 (SEQ ID NO: 15) and the mature light chain variable region has an amino acid sequence designated L1 (SEQ ID NO: 25).

17. The antibody of claim 4, wherein the mature heavy chain variable region has an amino acid sequence designated H3 (SEQ ID NO: 16) and the mature light chain variable region has an amino acid sequence designated L2 (SEQ ID NO: 26).

18. The antibody of claim 13, wherein the mature heavy chain variable region is fused to a heavy chain constant region having the sequence of SEQ ID NO: 34, 69, or 70 and/or the mature light chain variable region is fused to a light chain constant region having the sequence of SEQ ID NO: 36 or 72.

19. A pharmaceutical composition comprising an antibody as defined in claim 1 and a pharmaceutically-acceptable carrier.

* * * * *

SEQUENCE LISTING

```
<160> NUMBER OF SEQ ID NOS: 72

<210> SEQ ID NO 1
<211> LENGTH: 37
<212> TYPE: PRT
<213> ORGANISM: Homo Sapiens

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Cys Lys Lys Gly Gly Ala Ile Leu Ser Ser Thr Asn Val Gly Ser Asn
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

Cys Leu Ser Ser Thr Asn Val Gly Ser Asn Thr Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Leu Ser Ser Thr Asn Val Gly Ser Asn Thr Tyr
1               5                   10

<210> SEQ ID NO 5
<211> LENGTH: 399
<212> TYPE: DNA
<213> ORGANISM: Artificial Sequence
<220> FEATURE:
<223> OTHER INFORMATION: Synthetic
```

<400> SEQUENCE: 5

```
atggacttga gactgagctg tgctttattt attgttcttt taaaaggggt ccagagtgaa      60
gtgaagcttg aggagtctgg aggaggcttg gtgcaacctg gaggatccat gaaactctcc     120
tgtgttgcct ctggattcac tttcagtaac tactggatgt actgggtccg ccagtctcca     180
gagaagggac ttgagtgggt tgctgaaatt agattgaaat ctgataatta tgcaacacat     240
tatgcggagt ctgtgaaggg gaggttcacc atctcaagag atgattccaa aagtagtgtc     300
tacctgcaaa tgaacagctt aagggctgaa gacactggaa tttattactg cacaatcttt     360
gactactggg gccaaggcac cactctcaca gtctcctca                             399
```

<210> SEQ ID NO 6
<211> LENGTH: 133
<212> TYPE: PRT
<213> ORGANISM: Artificial Sequence
<220> FEATURE:
<223> OTHER INFORMATION: Synthetic

<400> SEQUENCE: 6

```
Met Asp Leu Arg Leu Ser Cys Ala Phe Ile Ile Val Leu Leu Lys Gly
  1               5                  10                  15
Val Gln Ser Glu Val Lys Leu Glu Glu Ser Gly Gly Gly Leu Val Gln
             20                  25                  30
Pro Gly Gly Ser Met Lys Leu Ser Cys Val Ala Ser Gly Phe Thr Phe
         35                  40                  45
Ser Asn Tyr Trp Met Tyr Trp Val Arg Gln Ser Pro Glu Lys Gly Leu
     50                  55                  60
Glu Trp Val Ala Glu Ile Arg Leu Lys Ser Asp Asn Tyr Ala Thr His
 65                  70                  75                  80
Tyr Ala Glu Ser Val Lys Gly Arg Phe Thr Ile Ser Arg Asp Asp Ser
                 85                  90                  95
Lys Ser Ser Val Tyr Leu Gln Met Asn Ser Leu Arg Ala Glu Asp Thr
            100                 105                 110
Gly Ile Tyr Tyr Cys Thr Ile Phe Asp Tyr Trp Gly Gln Gly Thr Thr
        115                 120                 125
Leu Thr Val Ser Ser
    130
```

<210> SEQ ID NO 7
<211> LENGTH: 393
<212> TYPE: DNA
<213> ORGANISM: Artificial Sequence
<220> FEATURE:
<223> OTHER INFORMATION: Synthetic

<400> SEQUENCE: 7

```
atgagtcctg cccagttcct gtttctgtta gtgctctgga ttcgggaaac caacggtgat      60
gttgtgatga cccagactcc actcactttg tcggttacca ttggacaacc agcctccatc     120
tcttgcaagt caagtcagag cctcttagat agtgatggaa agacatattt gaattggttg     180
ttacagaggc caggccagtc tccaaagcgc ctaatctatc tggtgtctaa actggactct     240
ggagtccctg acaggttcac tggcagtgga tcagggacag atttcacact gaaaatcagc     300
agagtggagg ctgaggattt gggagttcat tattgctggc aaggtagaca ttttccgtac     360
acgttcggag gggggaccaa gctggaaata aaa                                  393
```

<210> SEQ ID NO 8

```
<211> LENGTH: 131
<212> TYPE: PRT
<213> ORGANISM: Artificial Sequence
<220> FEATURE:
<223> OTHER INFORMATION: Synthetic

<400> SEQUENCE: 8

Met Ser Pro Ala Gln Phe Leu Phe Leu Leu Val Leu Trp Ile Arg Glu
 1               5                  10                  15

Thr Asn Gly Asp Val Val Met Thr Gln Thr Pro Leu Thr Leu Ser Val
            20                  25                  30

Thr Ile Gly Gln Pro Ala Ser Ile Ser Cys Lys Ser Ser Gln Ser Leu
        35                  40                  45

Leu Asp Ser Asp Gly Lys Thr Tyr Leu Asn Trp Leu Leu Gln Arg Pro
50                  55                  60

Gly Gln Ser Pro Lys Arg Leu Ile Tyr Leu Val Ser Lys Leu Asp Ser
65                  70                  75                  80

Gly Val Pro Asp Arg Phe Thr Gly Ser Gly Ser Gly Thr Asp Phe Thr
                85                  90                  95

Leu Lys Ile Ser Arg Val Glu Ala Glu Asp Leu Gly Val His Tyr Cys
            100                 105                 110

Trp Gln Gly Arg His Phe Pro Tyr Thr Phe Gly Gly Gly Thr Lys Leu
        115                 120                 125

Glu Ile Lys
    130

<210> SEQ ID NO 9
<211> LENGTH: 114
<212> TYPE: PRT
<213> ORGANISM: Artificial Sequence
<220> FEATURE:
<223> OTHER INFORMATION: Synthetic

<400> SEQUENCE: 9

Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Thr Phe Ser Asn Tyr
            20                  25                  30

Trp Met Tyr Trp Val Arg Gln Ser Pro Glu Lys Gly Leu Glu Trp Val
        35                  40                  45

Ala Glu Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Ile Phe Asp Tyr Trp Gly Gln Gly Thr Thr Val Thr Val
            100                 105                 110

Ser Ser

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Asn Tyr Trp Met Tyr
```

<210> SEQ ID NO 11
<211> LENGTH: 19
<212> TYPE: PRT
<213> ORGANISM: Artificial Sequence
<220> FEATURE:
<223> OTHER INFORMATION: Synthetic

<400> SEQUENCE: 11

Glu Ile Arg Leu Lys Ser Asp Asn Tyr Ala Thr His Tyr Ala Glu Ser
1               5                   10                  15

Val Lys Gly

<210> SEQ ID NO 12
<211> LENGTH: 3
<212> TYPE: PRT
<213> ORGANISM: Artificial Sequence
<220> FEATURE:
<223> OTHER INFORMATION: Synthetic

<400> SEQUENCE: 12

Phe Asp Tyr
1

<210> SEQ ID NO 13
<211> LENGTH: 114
<212> TYPE: PRT
<213> ORGANISM: Artificial Sequence
<220> FEATURE:
<223> OTHER INFORMATION: Synthetic

<400> SEQUENCE: 13

Leu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asp Ser Leu Lys Thr Glu Asp Thr Ala Val Tyr
                85                  90                  95

Tyr Cys Thr Thr Tyr Glu Gly Trp Gly Gln Gly Thr Leu Val Thr Val
            100                 105                 110

Ser Ser

<210> SEQ ID NO 14
<211> LENGTH: 114
<212> TYPE: PRT
<213> ORGANISM: Artificial Sequence
<220> FEATURE:
<223> OTHER INFORMATION: Synthetic

<400> SEQUENCE: 14

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
            35                  40                  45

Gly Glu Ile Arg Leu Lys Ser Asp Asn Tyr Ala Thr His Tyr Ala Glu
 50                  55                  60

Ser Val Lys Gly Arg Phe Thr Ile Ser Arg Asp Asp Ser Lys Asn Thr
 65                  70                  75                  80

Val Tyr Leu Gln Met Asp Ser Leu Lys Thr Glu Asp Thr Ala Val Tyr
                85                  90                  95

Tyr Cys Thr Ile Phe Asp Tyr Trp Gly Gln Gly Thr Leu Val Thr Val
            100                 105                 110

Ser Ser

<210> SEQ ID NO 15
<211> LENGTH: 114
<212> TYPE: PRT
<213> ORGANISM: Artificial Sequence
<220> FEATURE:
<223> OTHER INFORMATION: Synthetic

<400> SEQUENCE: 15

Glu Val Gln Leu Val Glu Ser Gly Gly Gly Leu Val Gln Pro Gly Gly
 1               5                   10                  15

Ser Leu Lys Leu Ser Cys Ala Ala Ser Gly Phe Thr Phe Ser Asn Tyr
                20                  25                  30

Trp Met Tyr Trp Val Arg Gln Ala Pro Gly Lys Gly Leu Glu Trp Val
            35                  40                  45

Gly Glu Ile Arg Leu Lys Ser Asp Asn Tyr Ala Thr His Tyr Ala Glu
 50                  55                  60

Ser Val Lys Gly Arg Phe Thr Ile Ser Arg Asp Asp Ser Lys Asn Thr
 65                  70                  75                  80

Ala Tyr Leu Gln Met Asp Ser Leu Lys Thr Glu Asp Thr Ala Val Tyr
                85                  90                  95

Tyr Cys Thr Thr Phe Asp Tyr Trp Gly Gln Gly Thr Leu Val Thr Val
            100                 105                 110

Ser Ser

<210> SEQ ID NO 16
<211> LENGTH: 114
<212> TYPE: PRT
<213> ORGANISM: Artificial Sequence
<220> FEATURE:
<223> OTHER INFORMATION: Synthetic

<400> SEQUENCE: 16

Glu Val Gln Leu Val Glu Ser Gly Gly Gly Leu Val Gln Pro Gly Gly
 1               5                   10                  15

Ser Leu Lys Leu Ser Cys Ala Ala Ser Gly Phe Thr Phe Ser Asn Tyr
                20                  25                  30

Trp Met Tyr Trp Val Arg Gln Ala Pro Gly Lys Gly Leu Glu Trp Val
            35                  40                  45

Gly Glu Ile Arg Leu Lys Ser Asp Asn Tyr Ala Thr His Tyr Ala Glu
 50                  55                  60

Ser Val Lys Gly Arg Phe Thr Ile Ser Arg Asp Asp Ser Lys Asn Thr
 65                  70                  75                  80

Ala Tyr Leu Gln Met Asp Ser Leu Lys Thr Glu Asp Thr Ala Val Tyr
                85                  90                  95

Tyr Cys Thr Ile Phe Asp Tyr Trp Gly Gln Gly Thr Leu Val Thr Val

Ser Ser

<210> SEQ ID NO 17
<211> LENGTH: 342
<212> TYPE: DNA
<213> ORGANISM: Artificial Sequence
<220> FEATURE:
<223> OTHER INFORMATION: Synthetic

<400> SEQUENCE: 17

```
gaggtgcagc tggtggagtc cggcggcggc ctggtgcagc ccggcggctc cctgaagctg      60
tcctgcgccg cctccggctt caccttctcc aactactgga tgtactgggt gcgccaggcc     120
cccggcaagg gcctggagtg ggtgggcgag atccgcctga agtccgacaa ctacgccacc     180
cactacgccg agtccgtgaa gggccgcttc accatctccc gcgacgactc caagaacacc     240
gtgtacctgc agatggactc cctgaagacc gaggacaccg ccgtgtacta ctgcaccatc     300
ttcgactact ggggccaggg caccctggtg accgtgtcct cc                        342
```

<210> SEQ ID NO 18
<211> LENGTH: 342
<212> TYPE: DNA
<213> ORGANISM: Artificial Sequence
<220> FEATURE:
<223> OTHER INFORMATION: Synthetic

<400> SEQUENCE: 18

```
gaggtgcagc tggtggagtc cggcggcggc ctggtgcagc ccggcggctc cctgaagctg      60
tcctgcgccg cctccggctt caccttctcc aactactgga tgtactgggt gcgccaggcc     120
cccggcaagg gcctggagtg ggtgggcgag atccgcctga agtccgacaa ctacgccacc     180
cactacgccg agtccgtgaa gggccgcttc accatctccc gcgacgactc caagaacacc     240
gcctacctgc agatggactc cctgaagacc gaggacaccg ccgtgtacta ctgcaccacc     300
ttcgactact ggggccaggg caccctggtg accgtgtcct cc                        342
```

<210> SEQ ID NO 19
<211> LENGTH: 342
<212> TYPE: DNA
<213> ORGANISM: Artificial Sequence
<220> FEATURE:
<223> OTHER INFORMATION: Synthetic

<400> SEQUENCE: 19

```
gaggtgcagc tggtggagtc cggcggcggc ctggtgcagc ccggcggctc cctgaagctg      60
tcctgcgccg cctccggctt caccttctcc aactactgga tgtactgggt gcgccaggcc     120
cccggcaagg gcctggagtg ggtgggcgag atccgcctga agtccgacaa ctacgccacc     180
cactacgccg agtccgtgaa gggccgcttc accatctccc gcgacgactc caagaacacc     240
gcgtacctgc agatggactc cctgaagacc gaggacaccg ccgtgtacta ctgcaccatc     300
ttcgactact ggggccaggg caccctggtg accgtgtcct cc                        342
```

<210> SEQ ID NO 20
<211> LENGTH: 112
<212> TYPE: PRT
<213> ORGANISM: Artificial Sequence
<220> FEATURE:
<223> OTHER INFORMATION: Synthetic

<400> SEQUENCE: 20

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val His Tyr Cys Trp Gln Gly
                85                  90                  95

Arg His Phe Pro Tyr Thr Phe Gly Gly Gly Thr Lys Leu Glu Ile Lys
                100                 105                 110
```

<210> SEQ ID NO 21
<211> LENGTH: 16
<212> TYPE: PRT
<213> ORGANISM: Artificial Sequence
<220> FEATURE:
<223> OTHER INFORMATION: Synthetic

<400> SEQUENCE: 21

```
Lys Ser Ser Gln Ser Leu Leu Asp Ser Asp Gly Lys Thr Tyr Leu Asn
1               5                   10                  15
```

<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

```
Leu Val Ser Lys Leu Asp Ser
1               5
```

<210> SEQ ID NO 23
<211> LENGTH: 9
<212> TYPE: PRT
<213> ORGANISM: Artificial Sequence
<220> FEATURE:
<223> OTHER INFORMATION: Synthetic

<400> SEQUENCE: 23

```
Trp Gln Gly Arg His Phe Pro Tyr Thr
1               5
```

<210> SEQ ID NO 24
<211> LENGTH: 112
<212> TYPE: PRT
<213> ORGANISM: Artificial Sequence
<220> FEATURE:
<223> OTHER INFORMATION: Synthetic

<400> SEQUENCE: 24

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr His Leu Asn Trp Phe Gln Gln Arg Pro Gly Gln Ser
        35                  40                  45
```

```
Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
               100                 105                 110
```

<210> SEQ ID NO 25
<211> LENGTH: 112
<212> TYPE: PRT
<213> ORGANISM: Artificial Sequence
<220> FEATURE:
<223> OTHER INFORMATION: Synthetic

<400> SEQUENCE: 25

```
Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Gln Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val His Tyr Cys Trp Gln Gly
                85                  90                  95

Arg His Phe Pro Tyr Thr Phe Gly Gln Gly Thr Lys Leu Glu Ile Lys
               100                 105                 110
```

<210> SEQ ID NO 26
<211> LENGTH: 112
<212> TYPE: PRT
<213> ORGANISM: Artificial Sequence
<220> FEATURE:
<223> OTHER INFORMATION: Synthetic

<400> SEQUENCE: 26

```
Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Gln Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                85                  90                  95

Arg His Phe Pro Tyr Thr Phe Gly Gln Gly Thr Lys Leu Glu Ile Lys
               100                 105                 110
```

<210> SEQ ID NO 27
<211> LENGTH: 112
<212> TYPE: PRT

<213> ORGANISM: Artificial Sequence
<220> FEATURE:
<223> OTHER INFORMATION: Synthetic

<400> SEQUENCE: 27

```
Asp Val Val Met Thr Gln Ser Pro Leu Ser Leu Pro Val Thr Leu Gly
1               5                   10                  15
Gln Pro Ala Ser Ile Ser Cys Lys Ser Ser Gln Ser Leu Leu Asp Ser
            20                  25                  30
Asp Gly Lys Thr Tyr Leu Asn Trp Phe Gln Gln Arg Pro Gly Gln Ser
        35                  40                  45
Pro Arg Arg Leu Ile Tyr Leu Val Ser Lys Leu Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Trp Gln Gly
                85                  90                  95
Arg His Phe Pro Tyr Thr Phe Gly Gln Gly Thr Lys Leu Glu Ile Lys
            100                 105                 110
```

<210> SEQ ID NO 28
<211> LENGTH: 112
<212> TYPE: PRT
<213> ORGANISM: Artificial Sequence
<220> FEATURE:
<223> OTHER INFORMATION: Synthetic

<400> SEQUENCE: 28

```
Asp Val Val Met Thr Gln Ser Pro Leu Ser Leu Pro Val Thr Leu Gly
1               5                   10                  15
Gln Pro Ala Ser Ile Ser Cys Lys Ser Ser Gln Ser Leu Leu Asp Ser
            20                  25                  30
Asp Gly Lys Thr Tyr Leu Asn Trp Phe Gln Gln Arg Pro Gly Gln Ser
        35                  40                  45
Pro Lys Arg Leu Ile Tyr Leu Val Ser Lys Leu Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val His Tyr Cys Trp Gln Gly
                85                  90                  95
Arg His Phe Pro Tyr Thr Phe Gly Gln Gly Thr Lys Leu Glu Ile Lys
            100                 105                 110
```

<210> SEQ ID NO 29
<211> LENGTH: 336
<212> TYPE: DNA
<213> ORGANISM: Artificial Sequence
<220> FEATURE:
<223> OTHER INFORMATION: Synthetic

<400> SEQUENCE: 29

```
gacgtggtga tgacccagtc cccctgtcc ctgcccgtga ccctgggcca gcccgcctcc    60
atctcctgca gtcctccca gtccctgctg gactccgacg gcaagaccta cctgaactgg   120
ctgcagcagc gccccggcca gtcccccaag cgcctgatct acctggtgtc caagctggac   180
tccggcgtgc ccgaccgctt ctccggctcc ggctccggca ccgacttcac cctgaagatc   240
tcccgcgtgg aggccgagga cgtgggcgtg cactactgct ggcagggccg ccacttcccc   300
tacaccttcg gccagggcac caagctggag atcaag                            336
```

<210> SEQ ID NO 30
<211> LENGTH: 336
<212> TYPE: DNA
<213> ORGANISM: Artificial Sequence
<220> FEATURE:
<223> OTHER INFORMATION: Synthetic

<400> SEQUENCE: 30

```
gacgtggtga tgacccagtc cccctgtcc ctgcccgtga ccctgggcca gcccgcctcc    60
atctcctgca agtcctccca gtccctgctg gactccgacg gcaagaccta cctgaactgg   120
ctgcagcagc gccccggcca gtcccccaag cgcctgatct acctggtgtc caagctggac   180
tccggcgtgc ccgaccgctt ctccggctcc ggctccggca ccgacttcac cctgaagatc   240
tcccgcgtgg aggccgagga cgtgggcgtg tactactgct ggcagggccg ccacttcccc   300
tacaccttcg gccagggcac caagctggag atcaag                             336
```

<210> SEQ ID NO 31
<211> LENGTH: 336
<212> TYPE: DNA
<213> ORGANISM: Artificial Sequence
<220> FEATURE:
<223> OTHER INFORMATION: Synthetic

<400> SEQUENCE: 31

```
gacgtggtga tgacccagtc cccctgtcc ctgcccgtga ccctgggcca gcccgcctcc    60
atctcctgca agtcctccca gtccctgctg gactccgacg gcaagaccta cctgaactgg   120
ttccagcagc gccccggcca gtccccccgc cgcctgatct acctggtgtc caagctggac   180
tccggcgtgc ccgaccgctt ctccggctcc ggctccggca ccgacttcac cctgaagatc   240
tcccgcgtgg aggccgagga cgtgggcgtg tactactgct ggcagggccg ccacttcccc   300
tacaccttcg gccagggcac caagctggag atcaag                             336
```

<210> SEQ ID NO 32
<211> LENGTH: 336
<212> TYPE: DNA
<213> ORGANISM: Artificial Sequence
<220> FEATURE:
<223> OTHER INFORMATION: Synthetic

<400> SEQUENCE: 32

```
gacgtggtga tgacccagtc cccctgtcc ctgcccgtga ccctgggcca gcccgcctcc    60
atctcctgca agtcctccca gtccctgctg gactccgacg gcaagaccta cctgaactgg   120
ttccagcagc gccccggcca gtcccccaag cgcctgatct acctggtgtc caagctggac   180
tccggcgtgc ccgaccgctt ctccggctcc ggctccggca ccgacttcac cctgaagatc   240
tcccgcgtgg aggccgagga cgtgggcgtg cactactgct ggcagggccg ccacttcccc   300
tacaccttcg gccagggcac caagctggag atcaag                             336
```

<210> SEQ ID NO 33
<211> LENGTH: 991
<212> TYPE: DNA
<213> ORGANISM: Artificial Sequence
<220> FEATURE:
<223> OTHER INFORMATION: Synthetic

<400> SEQUENCE: 33

```
gcctccacca agggcccatc ggtcttcccc ctggcaccct cctccaagag cacctctggg    60
```

```
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
acatctgcaa cgtgaatcac aagcccagca acaccaaggt ggacaagaga gttgagccca     300
aatcttgtga caaaactcac acatgcccac cgtgcccagc acctgaactc ctggggggac     360
cgtcagtctt cctcttcccc ccaaaaccca aggacaccct catgatctcc cggacccctg     420
aggtcacatg cgtggtggtg gacgtgagcc acgaagaccc tgaggtcaag ttcaactggt     480
acgtggacgg cgtggaggtg cataatgtca gacaaagcc gcgggaggag cagtacaaca     540
gcacgtaccg tgtggtcagc gtcctcaccg tcctgcacca ggactggctg aatggcaagg     600
agtacaagtg caaggtctcc aacaaagccc tcccagcccc catcgagaaa accatctcca     660
aagccaaagg gcagccccga gaaccacagg tgtacacgct gcccccatcc cgggaggaga     720
tgaccaagaa ccaggtcagc ctgacctgcc tggtcaaagg cttctatccc agcgacatcg     780
cgtggagtgg gagagcaatg ggcagccgga gaacaactac aagaccacgc ctcccgtgct     840
ggactccgac ggctccttct tcctctatag caagctcacc gtggacaaga gcaggtggca     900
gcaggggaac gtcttctcat gctccgtgat gcatgaggct ctgcacaacc actacacgca     960
gaagagcctc tccctgtccc cgggtaaatg a                                    991
```

<210> SEQ ID NO 34
<211> LENGTH: 330
<212> TYPE: PRT
<213> ORGANISM: Artificial Sequence
<220> FEATURE:
<223> OTHER INFORMATION: Synthetic
<400> SEQUENCE: 34

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
        195                 200                 205
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 35
<211> LENGTH: 321
<212> TYPE: DNA
<213> ORGANISM: Artificial Sequence
<220> FEATURE:
<223> OTHER INFORMATION: Synthetic

<400> SEQUENCE: 35
actgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat caggcctga gctcgcccgt cacaaagagc     300
ttcaacaggg gagagtgtta g                                               321

<210> SEQ ID NO 36
<211> LENGTH: 106
<212> TYPE: PRT
<213> ORGANISM: Artificial Sequence
<220> FEATURE:
<223> OTHER INFORMATION: Synthetic

<400> SEQUENCE: 36

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105
```

<210> SEQ ID NO 37
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 37

Xaa Gly Ser Gly Lys Cys Asn Thr Ala Thr Cys Ala Thr Gln Arg
 1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 38

Xaa Gly Ser Gly Cys Asn Thr Ala Thr Cys Ala Thr Gln Arg Leu
 1               5                  10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 39

Xaa Gly Ser Gly Asn Thr Ala Thr Cys Ala Thr Gln Arg Leu Ala
 1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 40

Xaa Gly Ser Gly Thr Ala Thr Cys Ala Thr Gln Arg Leu Ala Asn
 1               5                  10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

```
<400> SEQUENCE: 41

Xaa Gly Ser Gly Ala Thr Cys Ala Thr Gln Arg Leu Ala Asn Phe
 1               5                  10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 42

Xaa Gly Ser Gly Thr Cys Ala Thr Gln Arg Leu Ala Asn Phe Leu
 1               5                  10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 43

Xaa Gly Ser Gly Cys Ala Thr Gln Arg Leu Ala Asn Phe Leu Val
 1               5                  10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 44

Xaa Gly Ser Gly Ala Thr Gln Arg Leu Ala Asn Phe Leu Val His
 1               5                  10                  15

<210> SEQ ID NO 45
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 45

Xaa Gly Ser Gly Thr Gln Arg Leu Ala Asn Phe Leu Val His Ser
 1               5                  10                  15

<210> SEQ ID NO 46
<211> LENGTH: 15
<212> TYPE: PRT
<213> ORGANISM: Artificial Sequence
```

```
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 46

Xaa Gly Ser Gly Gln Arg Leu Ala Asn Phe Leu Val His Ser Ser
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 47

Xaa Gly Ser Gly Arg Leu Ala Asn Phe Leu Val His Ser Ser Asn
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 48

Xaa Gly Ser Gly Leu Ala Asn Phe Leu Val His Ser Ser Asn Asn
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 49

Xaa Gly Ser Gly Ala Asn Phe Leu Val His Ser Ser Asn Asn Phe
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 50

Xaa Gly Ser Gly Asn Phe Leu Val His Ser Ser Asn Asn Phe Gly
1               5                   10                  15
```

```
<210> SEQ ID NO 51
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 51

Xaa Gly Ser Gly Phe Leu Val His Ser Ser Asn Asn Phe Gly Ala
 1               5                  10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 52

Xaa Gly Ser Gly Leu Val His Ser Ser Asn Asn Phe Gly Ala Ile
 1               5                  10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 53

Xaa Gly Ser Gly Val His Ser Ser Asn Asn Phe Gly Ala Ile Leu
 1               5                  10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 54

Xaa Gly Ser Gly His Ser Ser Asn Asn Phe Gly Ala Ile Leu Ser
 1               5                  10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
```

<223> OTHER INFORMATION: Xaa = Ser with an N-terminal biotin group

<400> SEQUENCE: 55

Xaa Gly Ser Gly Ser Ser Asn Asn Phe Gly Ala Ile Leu Ser Ser
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 56

Xaa Gly Ser Gly Ser Asn Asn Phe Gly Ala Ile Leu Ser Ser Thr
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 57

Xaa Gly Ser Gly Asn Asn Phe Gly Ala Ile Leu Ser Ser Thr Asn
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 58

Xaa Gly Ser Gly Asn Phe Gly Ala Ile Leu Ser Ser Thr Asn Val
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 59

Xaa Gly Ser Gly Phe Gly Ala Ile Leu Ser Ser Thr Asn Val Gly
1               5                   10                  15

<210> SEQ ID NO 60
<211> LENGTH: 15
<212> TYPE: PRT

```
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 60

Xaa Gly Ser Gly Gly Ala Ile Leu Ser Ser Thr Asn Val Gly Ser
 1               5                  10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 61

Xaa Gly Ser Gly Ala Ile Leu Ser Ser Thr Asn Val Gly Ser Asn
 1               5                  10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group

<400> SEQUENCE: 62

Xaa Gly Ser Gly Ile Leu Ser Ser Thr Asn Val Gly Ser Asn Thr
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group
<220> FEATURE:
<221> NAME/KEY: VARIANT
<222> LOCATION: 15
<223> OTHER INFORMATION: Xaa = Tyr with C-terminal amidation

<400> SEQUENCE: 63

Xaa Gly Ser Gly Leu Ser Ser Thr Asn Val Gly Ser Asn Thr Xaa
 1               5                  10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa = Ser with an N-terminal biotin group
```

<400> SEQUENCE: 64

Xaa Gly Ser Gly Leu Ser Ser Thr Asn Val Gly Ser Asn Thr Tyr
1               5                   10                  15

<210> SEQ ID NO 65
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 11
<223> OTHER INFORMATION: Xaa = Arg with a C-terminal biotin group

<400> SEQUENCE: 65

Lys Cys Asn Thr Ala Thr Cys Ala Thr Gln Xaa
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Synthetic

<400> SEQUENCE: 66

Leu Ser Ser Thr Asn Val Gly Ser Asn Thr Tyr
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Synthetic

<400> SEQUENCE: 67

Ser Ser Thr Asn Val Gly Ser Asn Thr
1               5

<210> SEQ ID NO 68
<211> LENGTH: 990
<212> TYPE: DNA
<213> ORGANISM: Artificial Sequence
<220> FEATURE:
<223> OTHER INFORMATION: Synthetic

<400> SEQUENCE: 68

| | | | | | |
|---|---|---|---|---|---|
| gcctccacca | agggtccatc | ggtcttcccc | ctggcaccct | cctccaagag | cacctctggg | 60 |
| ggcacagcgg | ccctgggctg | cctggtcaag | gactacttcc | ccgaaccggt | gacggtgtcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacccagacc | 240 |
| tacatctgca | acgtgaatca | caagcccagc | aacaccaagg | tggacaagag | agttgagccc | 300 |
| aaatcttgtg | acaaaactca | cacatgccca | ccgtgcccag | cacctgaact | cctgggggga | 360 |
| ccgtcagtct | tcctcttccc | cccaaaaccc | aaggacaccc | tcatgatctc | ccggacccct | 420 |
| gaggtcacat | gcgtggtggt | ggacgtgagc | cacgaagacc | ctgaggtcaa | gttcaactgg | 480 |
| tacgtggacg | gcgtggaggt | gcataatgcc | aagacaaagc | cgcgggagga | gcagtacaac | 540 |
| agcacgtacc | gtgtggtcag | cgtcctcacc | gtcctgcacc | aggactggct | gaatggcaag | 600 |

```
gagtacaagt gcaaggtctc caacaaagcc ctcccagccc ccatcgagaa aaccatctcc    660
aaagccaaag gcagccccg  agaaccacag gtgtacaccc tgccccatc  ccggaggag     720 atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc cccgggtaaa                                     990
```

<210> SEQ ID NO 69
<211> LENGTH: 330
<212> TYPE: PRT
<213> ORGANISM: Artificial Sequence
<220> FEATURE:
<223> OTHER INFORMATION: Synthetic

<400> SEQUENCE: 69

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
                290                 295                 300
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 70
<211> LENGTH: 330
<212> TYPE: PRT
<213> ORGANISM: Artificial Sequence
<220> FEATURE:
<223> OTHER INFORMATION: Synthetic

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

<210> SEQ ID NO 71
<211> LENGTH: 321
<212> TYPE: DNA
<213> ORGANISM: Artificial Sequence
<220> FEATURE:
<223> OTHER INFORMATION: Synthetic

<400> SEQUENCE: 71

```
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                                321
```

<210> SEQ ID NO 72
<211> LENGTH: 107
<212> TYPE: PRT
<213> ORGANISM: Artificial Sequence
<220> FEATURE:
<223> OTHER INFORMATION: Synthetic

<400> SEQUENCE: 72

```
Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```